United States Patent

Toda

[11] Patent Number: 5,922,960
[45] Date of Patent: Jul. 13, 1999

[54] ULTRASONIC MATERIAL CONSTANT MEASURING SYSTEM

[76] Inventor: Kohji Toda, 1-49-18 Futaba, Yokosuka 239, Japan

[21] Appl. No.: 08/781,307

[22] Filed: Nov. 27, 1996

[51] Int. Cl.⁶ ............................ G01N 29/08; G01N 29/26
[52] U.S. Cl. ................................. 73/597; 73/599; 73/159; 73/1.86
[58] Field of Search ............................... 73/597, 598, 599, 73/600, 602, 624, 625, 628, 641, 159, 1.82, 1.86

[56] References Cited

U.S. PATENT DOCUMENTS

| | | | |
|---|---|---|---|
| 4,117,732 | 10/1978 | Brazhnikov | 73/599 |
| 4,366,712 | 1/1983 | Bäthmann et al. | 73/600 |
| 4,446,735 | 5/1984 | Weilacher | 73/597 |
| 4,612,807 | 9/1986 | Wunderer | 73/159 |
| 4,688,423 | 8/1987 | Orkosalo | 73/159 |
| 5,280,724 | 1/1994 | Higo et al. | 73/624 |
| 5,691,474 | 11/1997 | Gerz | 73/159 |

*Primary Examiner*—Michael Brock
*Assistant Examiner*—Rose M. Miller

[57] ABSTRACT

An ultrasonic material constant measuring system comprising a reference unit, an examination unit, at least a case equipped in at least the examination unit, and a signal processing unit. The reference unit consists of at least an input ultrasonic transducer $T_o$ and at least an output ultrasonic transducer $R_o$. The examination unit consists of at least an input ultrasonic transducer $T_s$ and at least an output ultrasonic transducer $R_s$. The case is placed between the ultrasonic transducers $T_s$ and $R_s$. The signal processing unit is connected with output terminals of the ultrasonic transducers $R_o$ and $R_s$. When electric signals are applied to the ultrasonic transducers $T_o$ and $T_s$, ultrasounds are emitted in air from the ultrasonic transducers $T_o$ and $T_s$, respectively, and then received by the ultrasonic transducers $R_o$ and $R_s$, respectively. If at least a sheet of paper is placed in case 1, the ultrasound emitted from ultrasonic transducer $T_s$ goes through the sheet of paper. Therefore, an output electric signal delivered from ultrasonic transducer $R_s$ is decreased, causing a difference between the output electric signal delivered from ultrasonic transducer $R_s$ and that delivered from ultrasonic transducer $R_o$. The difference is detected by signal processing unit 3 and compared with that corresponding to a standard paper. Thus, the thickness of the paper examined, or the number of sheets of the paper examined is evaluated.

4 Claims, 21 Drawing Sheets

ULTRASONIC MATERIAL CONSTANT MEASURING SYSTEM

BACKGROUND OF THE INVENTION

1. Field of the Invention

The present invention relates to an ultrasonic system for measuring material constant, that is, the thickness, the diameter or the number of materials, for example, the thickness of a paper, the thickness of a leaf, the diameter of a fiber, or the number of sheets of paper.

2. Description of the Prior Art

Conventional methods for measuring the number of sheets of paper are generally based on mechanical measurements. Accordingly, it is difficult to measure the number of sheets of paper precisely on the instant. A conventional method for measuring the thickness of a paper or the diameter of a fiber is based on mechanical measurements. Accordingly, it is difficult to measure the thickness of a paper or the diameter of a fiber continuously and quickly.

SUMMARY OF THE INVENTION

An object of the present invention is to provide an ultrasonic material constant measuring system capable of measuring the material constant under low power consumption and low voltage.

Another object of the present invention is to provide an ultrasonic material constant measuring system capable of measuring the material constant securely, precisely and quickly.

Another object of the present invention is to provide an ultrasonic material constant measuring system being easy to operate and maintain.

A still other object of the present invention is to provide an ultrasonic material constant measuring system excellent in durability.

A still further object of the present invention is to provide an ultrasonic material constant measuring system with a small size which is very light in weight and has a simple structure.

According to one aspect of the present invention there is provided an ultrasonic material constant measuring system comprising a reference unit, an examination unit, at least a case equipped in at least the examination unit, and a signal processing unit. The reference unit consists of at least an input ultrasonic transducer $T_o$ and at least an output ultrasonic transducer $R_o$ opposed to the ultrasonic transducer $T_o$. The examination unit consists of at least an input ultrasonic transducer $T_s$ and at least an output ultrasonic transducer $R_s$ opposed to the ultrasonic transducer $T_s$. The case is placed between the ultrasonic transducers $T_s$ and $R_s$, and has at least a sheet of paper, at least a leaf, or a fiber therein. The signal processing unit is connected with output terminals of the ultrasonic transducers $R_o$ and $R_s$.

When electric signals are applied to the ultrasonic transducers $T_o$ and $T_s$, respectively, ultrasounds are emitted in air from the ultrasonic transducer $T_o$ and $T_s$, respectively. The ultrasound emitted from the ultrasonic transducer $T_o$ is received by the ultrasonic transducer $R_o$, and delivered as an output electric signal from the ultrasonic transducer $R_o$. The ultrasound emitted from the ultrasonic transducer $T_s$ goes through the paper, the leaf or the fiber, and then, the ultrasound is received by the ultrasonic transducer $R_s$, and delivered as an output electric signal from the ultrasonic transducer $R_s$. Therefore, the output electric signal delivered from the ultrasonic transducer $R_s$ is decreased, causing a difference between the output electric signals delivered from the ultrasonic transducer $R_s$ and $R_o$. The difference is detected by the signal processing unit and compared with that corresponding to a standard paper, a standard leaf or a standard fiber. Thus, the thickness of a sheet of the paper examined, the number of sheets of the paper examined, the thickness of the leaf examined, or the diameter of the fiber examined is evaluated.

According to another aspect of the present invention there is provided an amplifier. An output terminal of the ultrasonic transducer $R_o$ is connected with input terminals of the ultrasonic transducers $T_o$ and $T_s$ via the amplifier. The ultrasonic transducers $T_o$, $R_o$ and the amplifier form an oscillator with an ultrasonic propagation lane, as a delay element, between the ultrasonic transducers $T_o$ and $R_o$.

According to another aspect of the present invention there is provided a signal processing unit comprising a phase comparator. The phase comparator detects a phase difference between the output electric signals delivered from the ultrasonic transducers $Ro$ and $R_s$, compares the phase difference with that corresponding to the standard paper, the standard leaf or the standard fiber, and evaluates the thickness of a sheet of the paper examined, the number of sheets of the paper examined, the thickness of the leaf examined, or the diameter of the fiber examined.

According to other aspect of the present invention there is provided an ultrasonic material constant measuring systems, wherein the direction of the ultrasound emitted from the ultrasonic transducer $T_s$ is oblique to an end surface of the paper examined or the leaf examined.

According to further aspect of the present invention there is provided an ultrasonic material constant measuring systems comprising a reference unit, an examination unit, and a signal processing unit. The reference unit consists of at least an input ultrasonic transducer $T_o$, at least an output ultrasonic transducer $R_o$ corresponding with the ultrasonic transducer $T_o$, and a reference case having a concavity therein. The examination unit consists of at least an input ultrasonic transducer $T_s$, at least an output ultrasonic transducer $R_s$ corresponding with the ultrasonic transducer $T_s$, and an examination case with a concavity therein and having at least a sheet of paper, at least a leaf, or a fiber on the concavity. The signal processing unit is connected with output terminals of the ultrasonic transducers $Ro$ and $Rs$.

When electric signals are applied to the ultrasonic transducers $T_o$ and $T_s$, respectively, ultrasounds are emitted in air from the ultrasonic transducer $T_o$ and $T_s$, respectively. The ultrasound emitted from the ultrasonic transducer $T_o$ is reflected by the concavity of the reference case, received by the ultrasonic transducer $R_o$, and delivered as an output electric signal from the ultrasonic transducer $R_o$. The ultrasound emitted from the ultrasonic transducer $T_s$ is reflected by the concavity of the examination case, received by the ultrasonic transducer $R_s$, and delivered as an output electric signal from the ultrasonic transducer $R_s$. In this time, the ultrasound emitted from the ultrasonic transducer $T_s$ goes through the paper, the leaf or the fiber twice. Therefore, the output electric signal delivered from the ultrasonic transducer $R_s$ is decreased, causing a difference between the output electric signals delivered from the ultrasonic transducer $R_s$ and $R_o$. The difference is detected by the signal processing unit and compared with that corresponding to a standard paper, a standard leaf or a standard fiber. Thus, the thickness of a sheet of the paper examined, the number of sheets of the paper examined, the thickness of the leaf examined, or the diameter of the fiber examined is evaluated.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
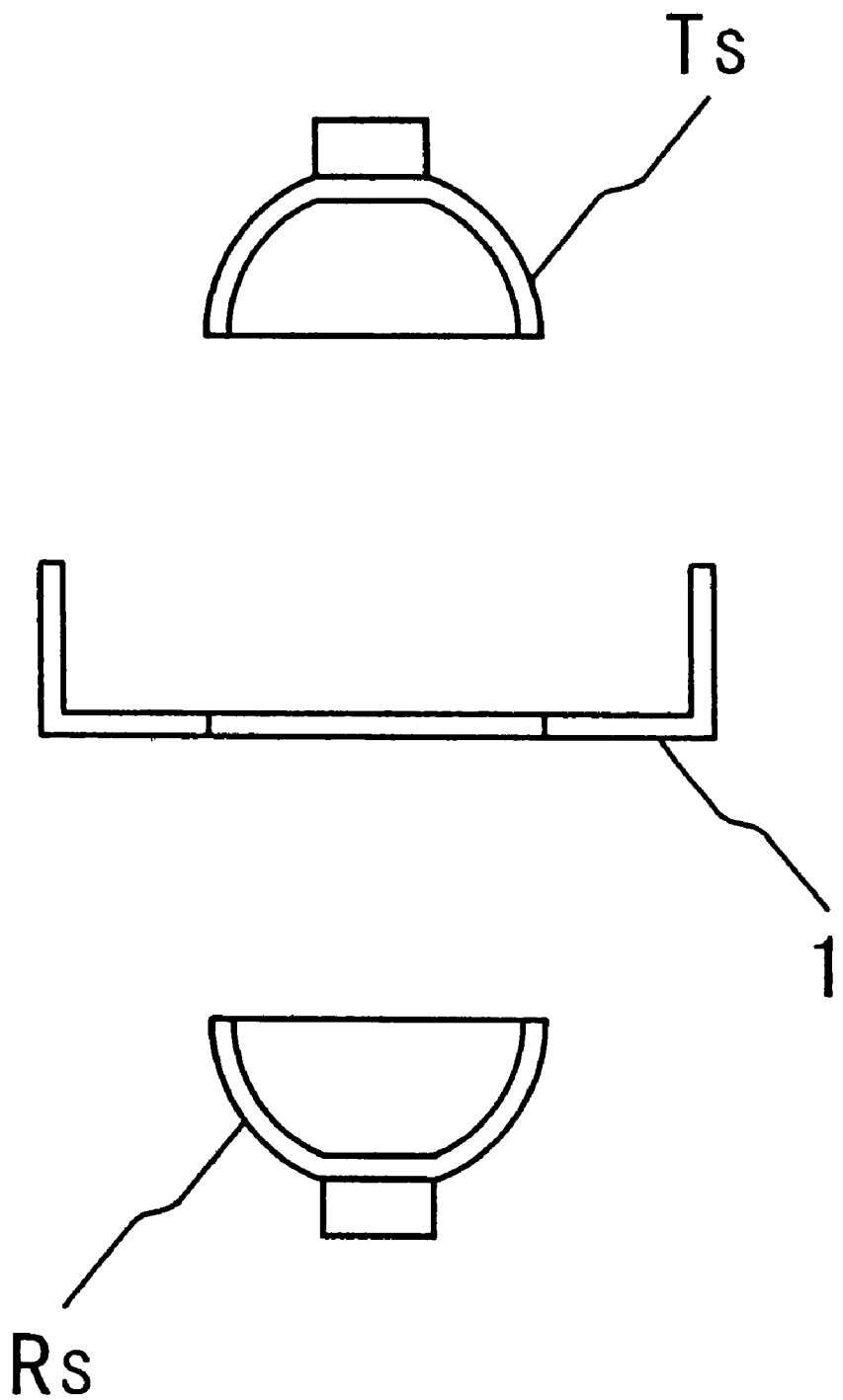
FIG. 1 shows a sectional view of an ultrasonic material constant measuring system according to a first embodiment of the present invention.

FIG. 1 shows a sectional view of an ultrasonic material constant measuring system according to a first embodiment of the present invention. The ultrasonic material constant measuring system comprises ultrasonic transducers $T_o$, $R_o$, $T_s$, $R_s$, case 1 placed between ultrasonic transducers $T_s$ and $R_s$, amplifier 2 and signal processing unit 3 comprising a differential amplifier. FIG. 1 shows only ultrasonic transducers $T_s$, $R_s$ and case 1. Ultrasonic transducers $T_o$, $R_o$, $T_s$ and $R_s$ are made from the same material each other, and have the same cone construction having the center frequency of 39.2 kHz and the cone diameter of 1 cm. Both the distance between ultrasonic transducers $T_o$ and $R_o$, and the distance between ultrasonic transducers $T_s$ and $R_s$ are 4.95 cm. Case 1 has a hole at the bottom thereof for the purpose of ultrasound transmission. If case 1 has no hole, it is necessary for case 1 to be made from a material such that an ultrasound is easy to go through the material. When operating, sheets of paper are placed in case 1. The relative position of ultrasonic transducer $T_o$ to ultrasonic transducer $R_o$ is equal to that of ultrasonic transducer $T_s$ to ultrasonic transducer $R_s$. Case 1 is not always placed between ultrasonic transducers $T_o$ and $R_o$.

Figure 2:
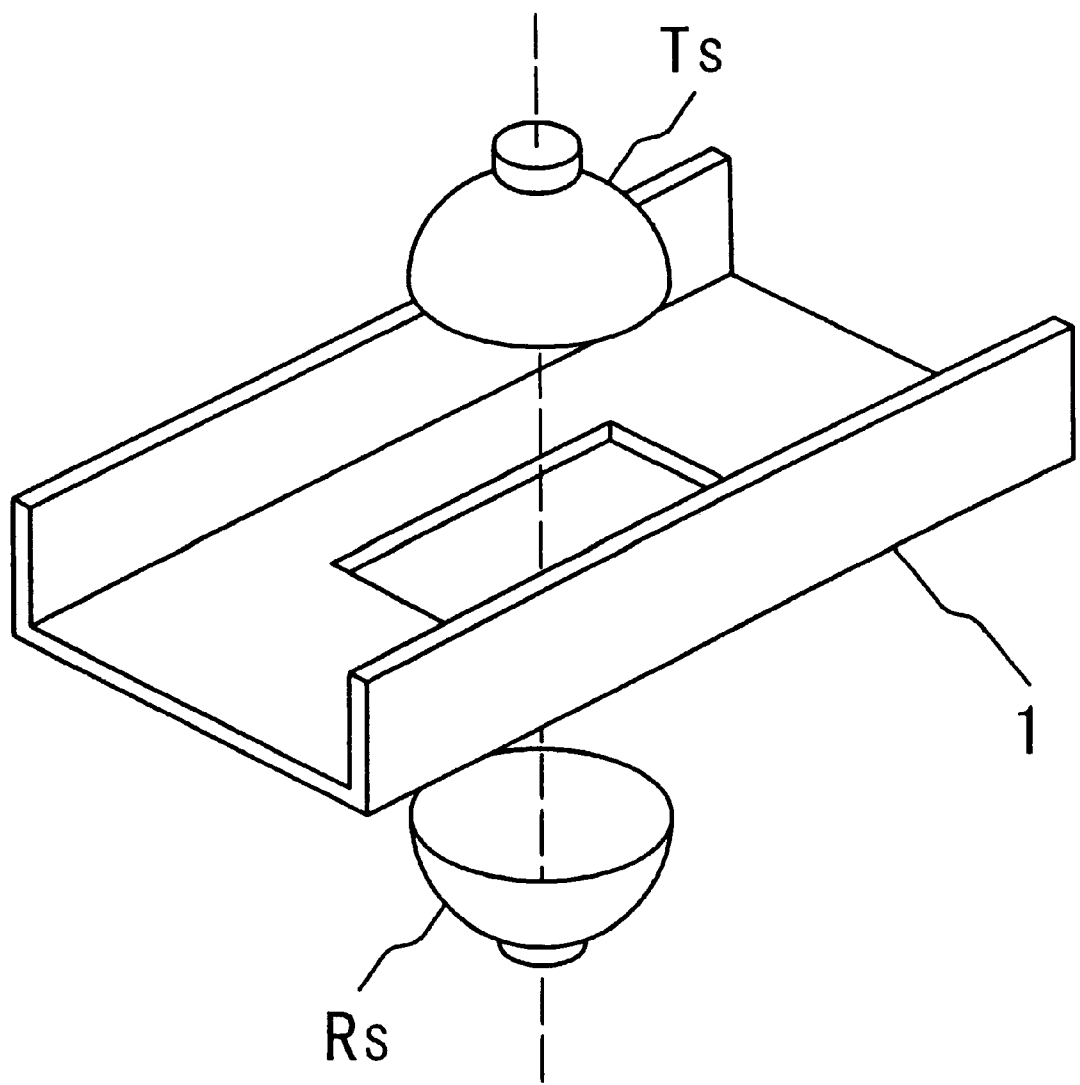
FIG. 2 shows a perspective view of ultrasonic transducers $T_s$, $R_s$ and case 1.

FIG. 2 shows a perspective view of ultrasonic transducers $T_s$, $R_s$ and case 1.

Figure 3:
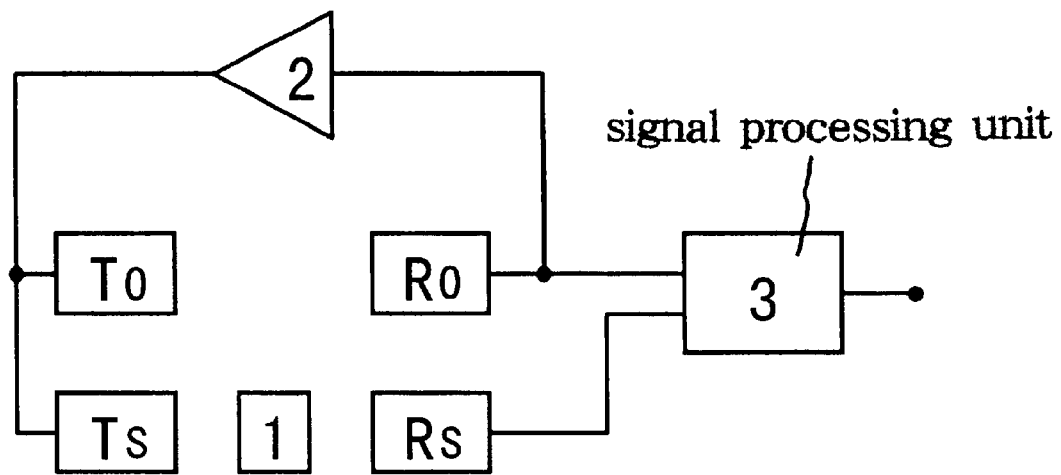
FIG. 3 shows a diagram of a driving circuit of the ultrasonic material constant measuring system in FIG. 1.

FIG. 3 shows a diagram of a driving circuit of the ultrasonic material constant measuring system in FIG. 1. Signal processing unit 3 to obtain an output electric signal is connected with output terminals of ultrasonic transducers $R_o$ and $R_s$. When operating the ultrasonic material constant measuring system in FIG. 1, an electric signal is applied to ultrasonic transducer $T_o$. In this time, an ultrasound is emitted in air from the cone center of ultrasonic transducer $T_o$. The ultrasound is received by ultrasonic transducer $R_o$, and is delivered as an output electric signal from ultrasonic transducer $R_o$. In the same way, when an electric signal is applied to ultrasonic transducer $T_s$, an ultrasound is emitted in air from the cone center of ultrasonic transducer $T_s$, and is received by ultrasonic transducer $R_s$ and delivered as an output electric signal from ultrasonic transducer $R_s$. If at least a sheet of paper is placed in case 1, the ultrasound emitted from ultrasonic transducer $T_s$ goes through the sheet of paper such that the direction of the ultrasound is vertical to an end surface of the paper. In this time, the output electric signal delivered from ultrasonic transducer $R_s$ is decreased, causing a difference between the output electric signal delivered from ultrasonic transducer $R_s$ and that delivered from ultrasonic transducer $R_o$. The difference is detected by signal processing unit 3 and compared with that corresponding to a standard paper. Thus, the thickness of the paper examined, or the number of sheets of the paper examined is evaluated. If signal processing unit 3 comprises a phase comparator to obtain an output electric signal detected in the form of phase comparison, a phase difference between the output electric signal delivered from ultrasonic transducer $R_s$ and that delivered from ultrasonic transducer $R_o$ is detected. Accordingly, the thickness of the paper examined, or the number of sheets of the paper examined is evaluated by comparing the phase difference with that corresponding to a standard paper. In the same way, if a leaf or a fiber is placed in case 1, the thickness of the leaf or the diameter of the fiber is obtained, respectively. An output terminal of ultrasonic transducer $R_o$ is connected with input terminals of ultrasonic transducers $T_o$ and $T_s$ via amplifier 2. Thus, ultrasonic transducers $T_o$, $R_o$ and amplifier 2 form an oscillator with an ultrasonic propagation lane, as a delay element, between the cone center of ultrasonic transducer $T_o$ and that of ultrasonic transducer $R_o$. The oscillator enables the ultrasonic material constant measuring system in FIG. 1 to have a small-sized circuit with a simple structure. The small-sized circuit causes the ultrasonic material constant measuring system to have a small size which is very light in weight, and to be operated under low power consumption and low voltage.

Figure 4:
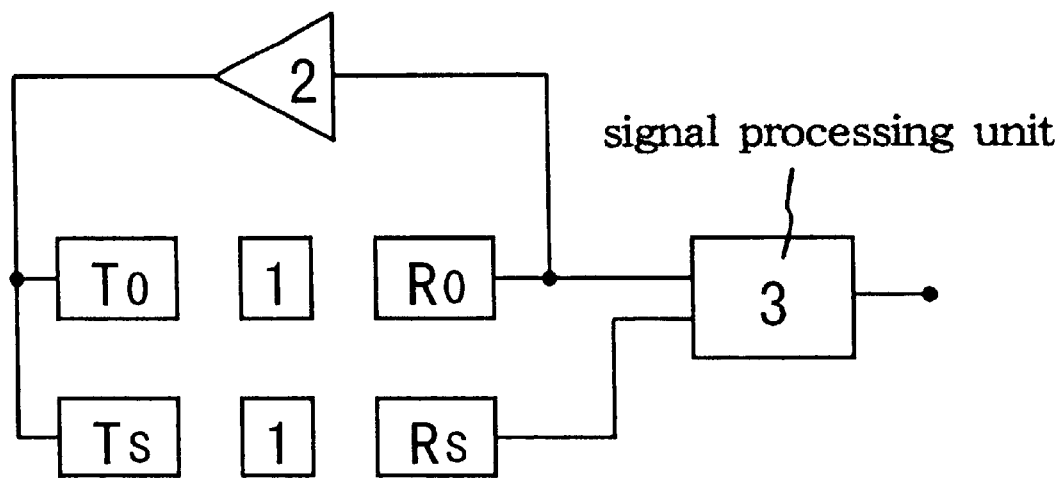
FIG. 4 shows a diagram of a driving circuit in case that another case 1 is placed between ultrasonic transducers $T_o$ and $R_o$ in the driving circuit in FIG. 3.

FIG. 4 shows a diagram of a driving circuit in case that another case 1 is placed between ultrasonic transducers $T_o$ and $R_o$ in the driving circuit in FIG. 3. When sheets of paper examined are placed in case 1 between ultrasonic transducers $T_s$ and $R_s$, and sheets of standard paper are placed in case 1 between ultrasonic transducers $T_o$ and $R_o$, a difference between the number of sheets of the paper examined and that of the standard paper is related to a difference between the output electric signals delivered from ultrasonic transducer $R_s$ and $R_o$.

Figure 5:
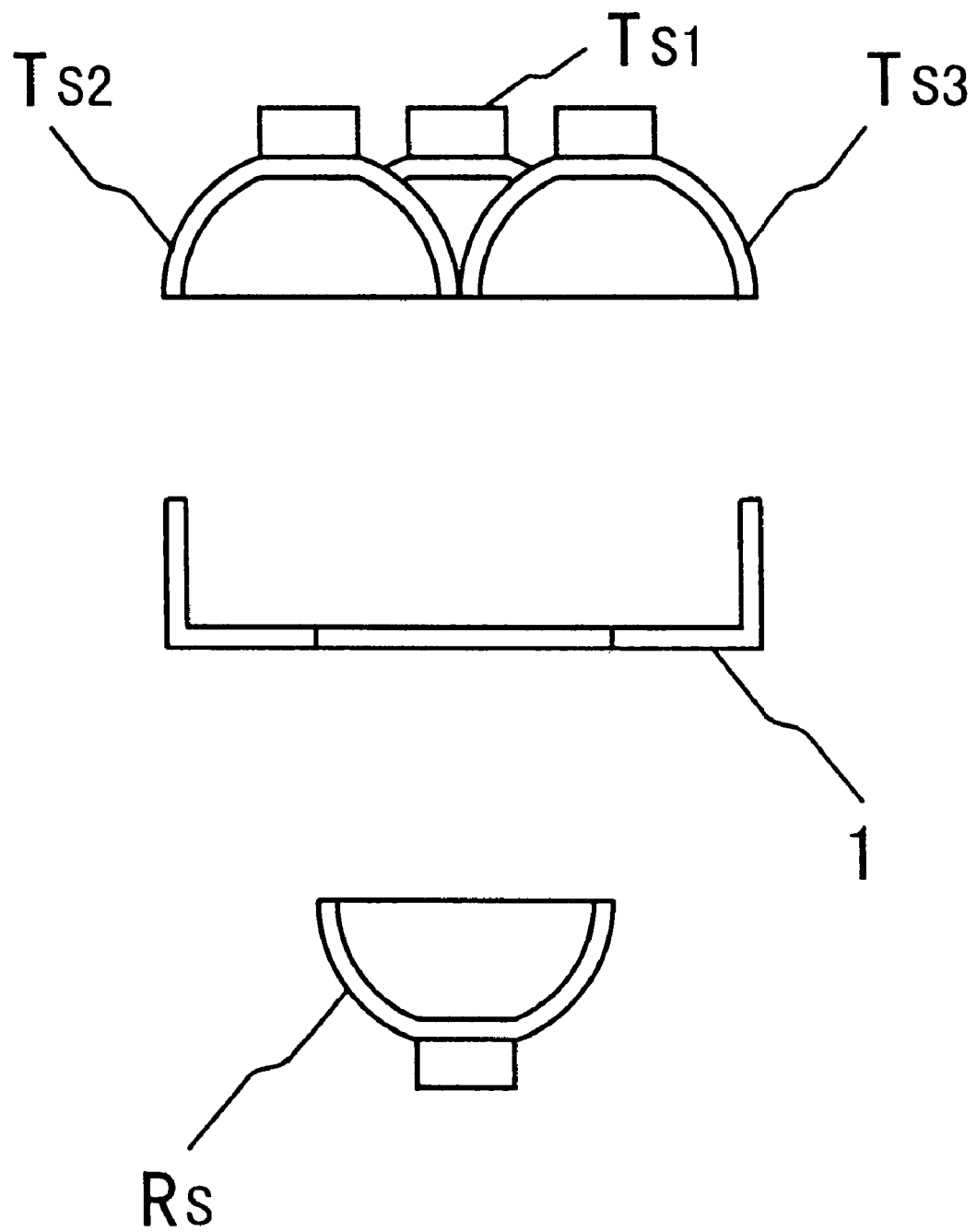
FIG. 5 shows a sectional view of an ultrasonic material constant measuring system according to a second embodiment of the present invention.

FIG. 5 shows a sectional view of an ultrasonic material constant measuring system according to a second embodiment of the present invention. The ultrasonic material constant measuring system comprises ultrasonic transducers $T_{o1}$, $T_{o2}$, $T_{o3}$, $T_{s1}$, $T_{s2}$, $T_{s3}$, $R_o$, $R_s$, case 1 placed between ultrasonic transducers $T_{s1}$, $T_{s2}$, $T_{s3}$ and ultrasonic transducer $R_s$, amplifier 2 and signal processing unit 3 comprising a differential amplifier. FIG. 5 shows only ultrasonic transducers $T_{s1}$, $T_{s2}$, $T_{s3}$, $R_s$ and case 1. Ultrasonic transducers $T_{o1}$, $T_{o2}$, $T_{o3}$, $T_{s1}$, $T_{s2}$ and $T_{s3}$ are made from the same material as ultrasonic transducer $T_o$, and have the same cone construction having the center frequency of 39.2 kHz and the cone diameter of 1 cm. Three gravity centers of ultrasonic transducers $T_{o1}$, $T_{o2}$, and $T_{o3}$ make a triangle, and ultrasonic transducer $R_o$ is opposed to the center of the triangle, the distance between ultrasonic transducers $T_{o1}$, $T_{o2}$, $T_{o3}$ and ultrasonic transducer $R_s$ being 4.95 cm. Three gravity centers of ultrasonic transducers $T_{s1}$, $T_{s2}$, $T_{s3}$ make a triangle, and ultrasonic transducer $R_s$ is opposed to the center of the triangle, the distance between ultrasonic transducers $T_{s1}$, $T_{s2}$, $T_{s3}$ and ultrasonic transducer $R_s$ being 4.95 cm. The relative position of ultrasonic transducers $T_{o1}$, $T_{o2}$ and $T_{o3}$ to ultrasonic transducer $R_o$ is equal to that of ultrasonic transducers $T_{s1}$, $T_{s2}$ and $T_{s3}$ to ultrasonic transducer $R_s$. Case 1 is not always placed between ultrasonic transducers $T_{o1}$, $T_{o2}$, $T_{o3}$ and ultrasonic transducer $R_o$.

Figure 6:
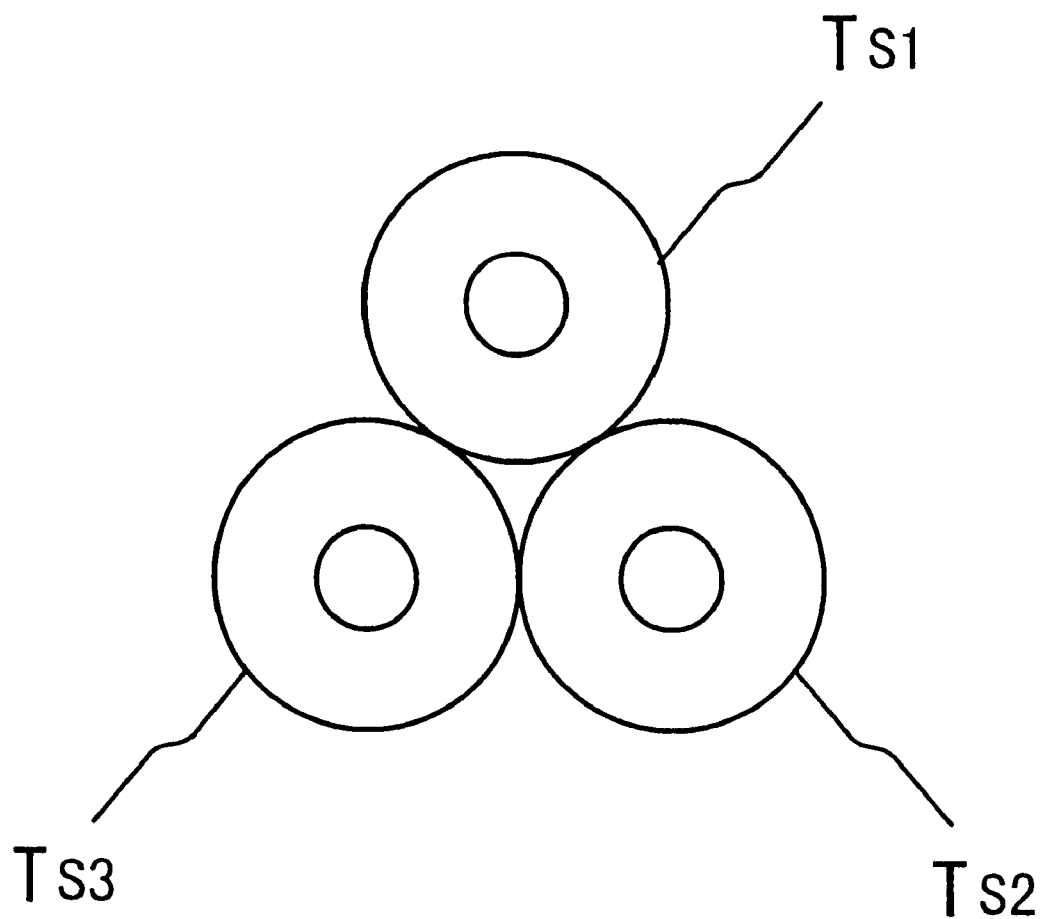
FIG. 6 shows a plan view of ultrasonic transducers $T_{s1}$, $T_{s2}$ and $T_{s3}$ viewed from case 1.

FIG. 6 shows a plan view of ultrasonic transducers $T_{s1}$, $T_{s2}$ and $T_{s3}$ viewed from case 1.

Figure 7:
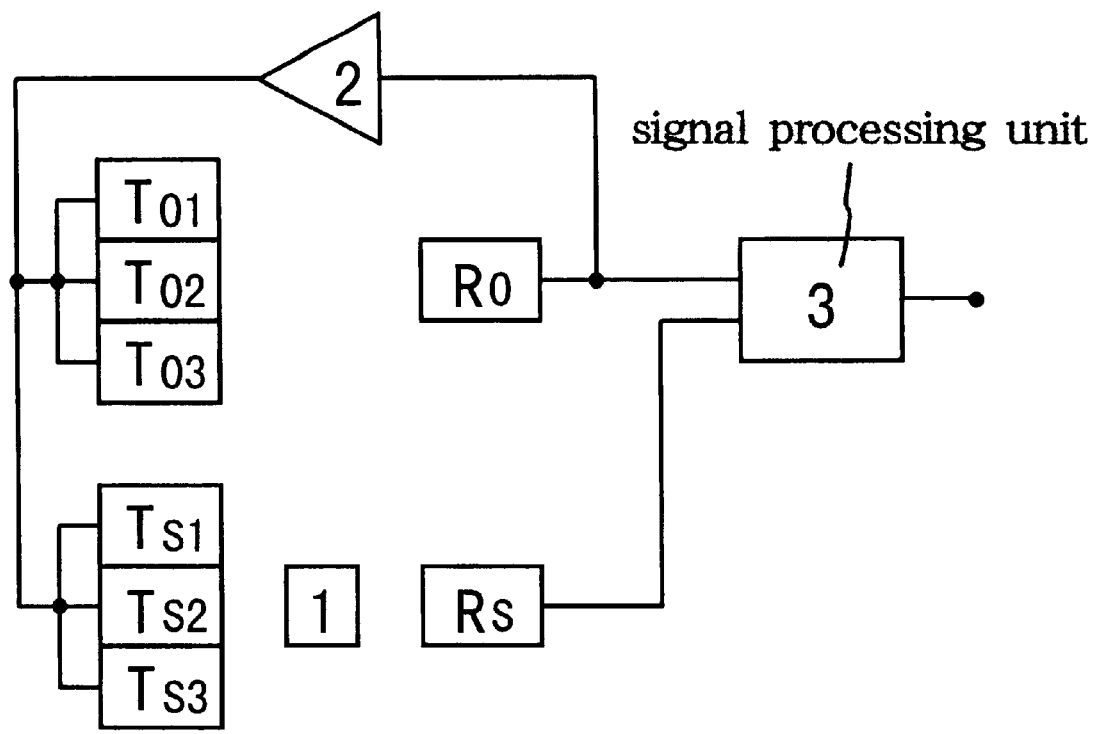
FIG. 7 shows a diagram of a driving circuit of the ultrasonic material constant measuring system in FIG. 5.

FIG. 7 shows a diagram of a driving circuit of the ultrasonic material constant measuring system in FIG. 5. Signal processing unit 3 is connected with output terminals of ultrasonic transducers $R_o$ and $R_s$. When operating the ultrasonic material constant measuring system in FIG. 5, electric signals are applied to ultrasonic transducers $T_{o1}$, $T_{o2}$ and $T_{o3}$, respectively. In this time, an ultrasound with a sharp directionality is emitted in air from the center of the triangle made by ultrasonic transducers $T_{o1}$, $T_{o2}$ and $T_{o3}$. The ultrasound is received by ultrasonic transducer $R_o$, and is delivered as an output electric signal from ultrasonic transducer $R_o$. In the same way, when electric signals are applied to ultrasonic transducers $T_{s1}$, $T_{s2}$ and $T_{s3}$, respectively, an ultrasound with a sharp directionality is emitted in air from the center of the triangle made by ultrasonic transducers $T_{s1}$, $T_{s2}$ and $T_{s3}$, and is received by ultrasonic transducer $R_s$ and delivered as an output electric signal from ultrasonic transducer $R_s$. Case 1 is placed at the area where the ultrasound emitted from ultrasonic transducers $T_{s1}$, $T_{s2}$ and $T_{s3}$, and is most sharply and most strongly. If at least a sheet of paper is placed in case 1, the ultrasound emitted from ultrasonic transducers $T_{s1}$, $T_{s2}$ and $T_{s3}$ goes through the sheet of paper such that the direction of the ultrasound is vertical to an end surface of the paper. In this time, the output electric signal delivered from ultrasonic transducer $R_s$ is decreased, causing a difference between the output electric signal delivered from ultrasonic transducer $R_s$ and that delivered from ultrasonic transducer $R_o$. The difference is detected by signal processing unit 3 and compared with that corresponding to a standard paper. Thus, the thickness of the paper examined, or the number of sheets of the paper examined is evaluated. If signal processing unit 3 comprises a phase comparator, a phase difference between the output electric signal delivered from ultrasonic transducer $R_s$ and that delivered from ultrasonic transducer $R_o$ is detected. Accordingly, the thickness of the paper examined, or the number of sheets of the paper examined is evaluated by comparing the phase difference with that corresponding to a standard paper. In the same way, if a leaf or a fiber is placed in case 1, the thickness of the leaf or the diameter of the fiber is obtained, respectively. The ultrasonic material constant measuring system in FIG. 5 enables a higher sensitive operation under a low voltage in comparison with that in FIG. 1, owing to input ultrasonic transducers emitting an ultrasound with a sharp directionality. An output terminal of ultrasonic transducer $R_o$ is connected with input terminals of ultrasonic transducers $T_{o1}$, $T_{o2}$, $T_{o3}$, $T_{s1}$, $T_{s2}$ and $T_{s3}$ via amplifier 2. Thus, ultrasonic transducers $T_{o1}$, $T_{o2}$, $T_{o3}$, $R_o$ and amplifier 2 form an oscillator with an ultrasonic propagation lane, as a delay element, between the center of the triangle made by ultrasonic transducers $T_{o1}$, $T_{o2}$ and $T_{o3}$, and the cone center of ultrasonic transducer $R_o$. The oscillator enables the ultrasonic material constant measuring system in FIG. 5 to have a small-sized circuit with a simple structure. The small-sized circuit causes the ultrasonic material constant measuring system to have a small size which is very light in weight, and to be operated under low power consumption and low voltage. If another case 1 is placed between ultrasonic transducers $T_{o1}$, $T_{o2}$, $T_{o3}$ and ultrasonic transducer $R_o$ in the driving circuit in FIG. 7, sheets of paper examined are placed in case 1 between ultrasonic transducers $T_s$ and $R_s$, and sheets of standard paper are placed in case 1 between ultrasonic transducers $T_o$ and $R_o$. In this time, a difference between the number of sheets of the paper examined and that of the standard paper is related to a difference between the output electric signals delivered from ultrasonic transducer $R_s$ and $R_o$.

Figure 8:
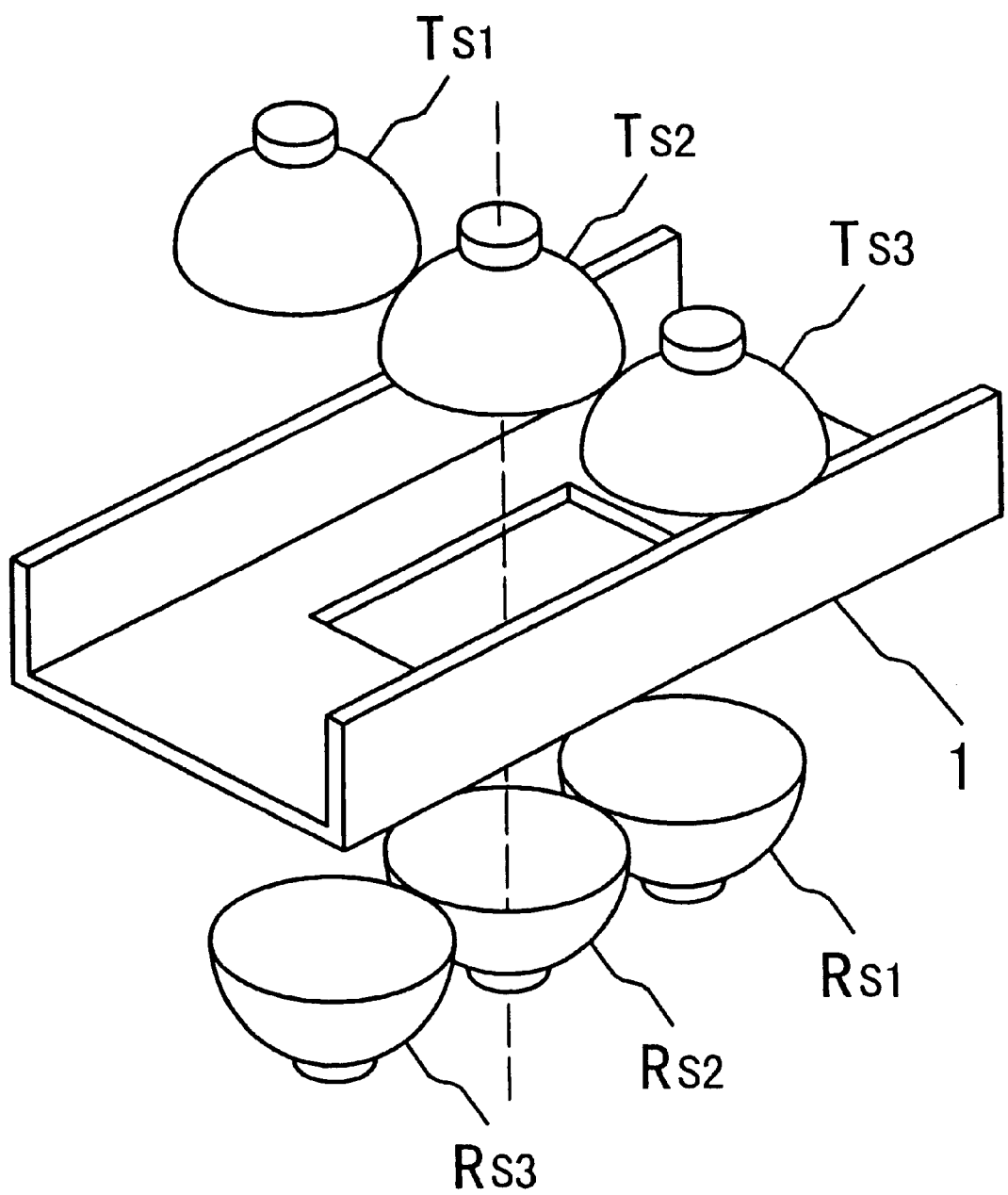
FIG. 8 shows a perspective view of an ultrasonic material constant measuring system according to a third embodiment of the present invention.

FIG. 8 shows a perspective view of an ultrasonic material constant measuring system according to a third embodiment of the present invention. The ultrasonic material constant measuring system comprises ultrasonic transducers $T_{o1}$, $T_{o2}$, $T_{o3}$, $T_{s1}$, $T_{s2}$, $T_{s3}$, $R_{o1}$, $R_{o2}$, $R_{o3}$, $R_{s1}$, $R_{s2}$, $R_{s3}$, case 1, amplifier 2 and signal processing unit 3 comprising a differential amplifier. Case 1 is placed between ultrasonic transducers $T_{s1}$, $T_{s2}$ and $T_{s3}$, and ultrasonic transducers $R_{s1}$, $R_{s2}$ and $R_{s3}$. FIG. 8 shows only ultrasonic transducers $T_{s1}$, $T_{s2}$, $T_{s3}$, $R_{s1}$, $R_{s2}$, $R_{s3}$ and case 1. Ultrasonic transducers $R_{o1}$, $R_{o2}$, $R_{o3}$, $R_{s1}$, $R_{s2}$ and $R_{s3}$ are made from the same material as ultrasonic transducer $T_o$, and have the same cone construction having the center frequency of 39.2 kHz and the cone diameter of 1 cm. Ultrasonic transducers $T_{o1}$, $T_{o2}$ and $T_{o3}$ are arranged such that three gravity centers thethereof make a straight line, and ultrasonic transducers $R_{o1}$, $R_{o2}$, $R_{o3}$ are arranged such that three gravity centers thereof make a straight line. The straight line made by ultrasonic transducers $T_{o1}$, $T_{o2}$ and $T_{o3}$ is vertical to the straight line made by ultrasonic transducers $R_{o1}$, $R_{o2}$ and $R_{o3}$, the distance between ultrasonic transducers $T_{o1}$, $T_{o2}$, $T_{o3}$ and ultrasonic transducers $R_{o1}$, $R_{o2}$, $R_{o3}$ being 4.95 cm. Ultrasonic transducers $T_{s1}$, $T_{s2}$ and $T_{s3}$ are arranged such that three gravity centers thereof make a straight line, and ultrasonic transducers $R_{s1}$, $R_{s2}$ and $R_{s3}$ are arranged such that three gravity centers thereof make a straight line. The straight line made by ultrasonic transducers $T_{s1}$, $T_{s2}$ and $T_{s3}$ is vertical to the straight line made by ultrasonic transducers $R_{s1}$, $R_{s2}$ and $R_{s3}$, the distance between ultrasonic transducers $T_{s1}$, $T_{s2}$, $T_{s3}$ and ultrasonic transducers $R_{s1}$, $R_{s2}$, $R_{s3}$ being 4.95 cm. The relative position of ultrasonic transducers $T_{o1}$, $T_{o2}$ and $T_{o3}$ to ultrasonic transducers $R_{o1}$, $R_{o2}$ and $R_{o3}$ is equal to that of ultrasonic transducers $T_{s1}$, $T_{s2}$ and $T_{s3}$ to ultrasonic transducers $R_{s1}$, $R_{s2}$ and $R_{s3}$. Case 1 is not always placed between ultrasonic transducers $T_{o1}$, $T_{o2}$, $T_{o3}$ and ultrasonic transducers $R_{o1}$, $R_{o2}$, $R_{o3}$.

Figure 9:
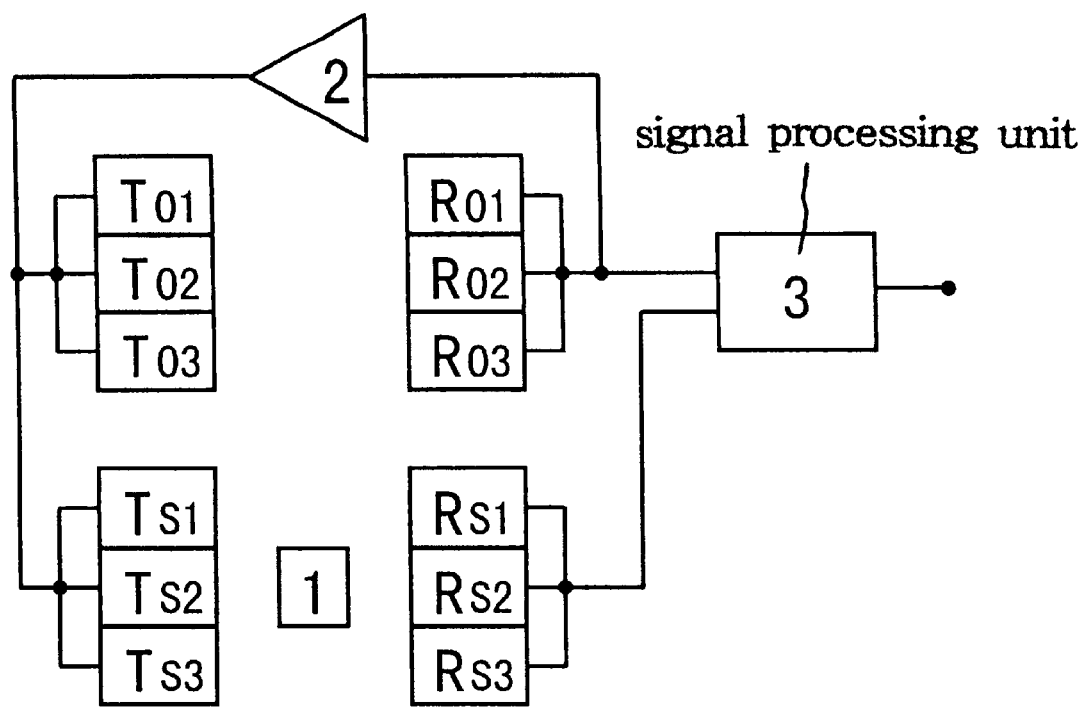
FIG. 9 shows a diagram of a driving circuit of the ultrasonic material constant measuring system in FIG. 8.

FIG. 9 shows a diagram of a driving circuit of the ultrasonic material constant measuring system in FIG. 8. Signal processing unit 3 is connected with a point linking three output terminals of ultrasonic transducers $R_{o1}$, $R_{o2}$ and $R_{o3}$, and a point linking three output terminals of ultrasonic transducers $R_{s1}$, $R_{s2}$ and $R_{s3}$. When operating the ultrasonic material constant measuring system in FIG. 8, electric signals are applied to ultrasonic transducers $T_{o1}$, $T_{o2}$ and $T_{o3}$. respectively, then an ultrasound with a sharp directionality is emitted in air from the center of the straight line made by ultrasonic transducers $T_{o1}$, $T_{o2}$ and $T_{o3}$. The ultrasound is received by ultrasonic transducers $R_{o1}$, $R_{o2}$ and $R_{o3}$, and is delivered as output electric signals from ultrasonic transducers $R_{o1}$, $R_{o2}$ and $R_{o3}$, respectively. In this time, ultrasonic transducers $T_{o1}$, $T_{o2}$ and $T_{o3}$ has an ability to emit an ultrasound with a directionality on a surface including three gravity centers of ultrasonic transducers $T_{o1}$, $T_{o3}$ and $R_{o2}$, and ultrasonic transducers $R_{o1}$, $R_{o2}$ and $R_{o3}$ has an ability to receive an ultrasound with a directionality on a surface including three gravity centers of ultrasonic transducers $T_{o2}$, $R_{o1}$ and $R_{o3}$. In the same way, when electric signals are applied to ultrasonic transducers $T_{s1}$, $T_{s2}$ and $T_{s3}$, respectively, an ultrasound with a sharp directionality is emitted in air from the center of the straight line made by ultrasonic transducers $T_{s1}$, $T_{s2}$ and $T_{s3}$, the ultrasound being received by ultrasonic transducers $R_{s1}$, $R_{s2}$ and $R_{s3}$ and delivered as output electric signals from ultrasonic transducers $R_{s1}$, $R_{s2}$ and $R_{s3}$, respectively. In this time, ultrasonic transducers $T_{s1}$, $T_{s2}$ and $T_{s3}$ has an ability to emit an ultrasound with a directionality on a surface including three gravity centers of ultrasonic transducers $T_{s1}$, $T_{s3}$ and $R_{s2}$, and ultrasonic transducers $R_{o1}$, $R_{s2}$, and $R_{s3}$ has an ability to receive an ultrasound with a directionality on a surface including three gravity centers of ultrasonic transducers $T_{s2}$, $R_{s1}$ and $R_{s3}$. Case 1 is placed at the area where the ultrasound emitted from ultrasonic transducers $T_{s1}$, $T_{s2}$ and $T_{s3}$ is most sharply and most strongly. If at least a sheet of paper is placed in of case 1, the ultrasound emitted from ultrasonic transducers $T_{s1}$, $T_{s2}$ and $T_{s3}$ goes through the sheet of paper such that the direction of the ultrasound is vertical to an end surface of the paper. In this time, an output electric signal delivered from the point linking output terminals of ultrasonic transducers $R_{s1}$, $R_{s2}$ and $R_{s3}$ is decreased, causing a difference between the output electric signal delivered from the point linking output terminals of ultrasonic transducers $R_{s1}$, $R_{s2}$, $R_{s3}$ and that delivered from the point linking output terminals of ultrasonic transducers $R_{o1}$, $R_{o2}$ and $R_{o3}$. The difference is detected by signal processing unit 3 and compared with that corresponding to a standard paper. Thus, the thickness of the paper examined, or the number of sheets of the paper examined is evaluated. If signal processing unit 3 comprises a phase comparator, a phase difference between the output electric signal delivered from the point linking output terminals of ultrasonic transducers $R_{s1}$, $R_{s2}$, $R_{s3}$ and that delivered from the point linking output terminals of ultrasonic transducers $R_{o1}$, $R_{o2}$, $R_{o3}$ is detected. Accordingly, the thickness of the paper examined, or the number of sheets of the paper examined is evaluated by comparing the phase difference with that corresponding to a standard paper. In the same way, if a leaf or a fiber is placed in case 1, the thickness of the leaf or the diameter of the fiber is obtained, respectively. The ultrasonic material constant measuring system in FIG. 8 enables a higher sensitive operation under a low voltage in comparison with that in FIG. 1, because of input ultrasonic transducers emitting an ultrasound with a sharp directionality, and output ultrasonic transducers receiving an ultrasound with a sharp directionality. The point linking output terminals of ultrasonic transducers $R_{o1}$, $R_{o2}$ and $R_{o3}$ is connected with input terminals of ultrasonic transducers $T_{o1}$, $T_{o2}$, $T_{o3}$, $T_{s1}$, $T_{s2}$ and $T_{s3}$ via amplifier 2. Thus, ultrasonic transducers $T_{o1}$, $T_{o2}$, $T_{o3}$, $R_{o1}$, $R_{o2}$, $R_{o3}$ and amplifier 2 form an oscillator with an ultrasonic propagation lane, as a delay element, between the center of the straight line made by ultrasonic transducers $T_{o1}$, $T_{o2}$ and $T_{o3}$, and the center of the straight line made by ultrasonic transducer $R_{o1}$, $R_{o2}$ and $R_{o3}$. The oscillator enables the ultrasonic material constant measuring system in FIG. 8 to have a small-sized circuit with a simple structure. The small-sized circuit causes the ultrasonic material constant measuring system to have a small size which is very light in weight, and to be operated under low power consumption and low voltage. If another case 1 is placed between ultrasonic transducers $T_{o1}$, $T_{o2}$, $T_{o3}$ and ultrasonic transducers $R_{o1}$, $R_{o2}$ and $R_{o3}$ in the driving circuit in FIG. 9, sheets of paper examined are placed in case 1 between ultrasonic transducers $T_{s1}$, $T_{s2}$, $T_{s3}$ and ultrasonic transducers $R_{s1}$, $R_{s2}$, $R_{s3}$, and sheets of standard paper are placed in case 1 between ultrasonic transducers $T_{o1}$, $T_{o2}$, $T_{o3}$ and ultrasonic transducers $R_{o1}$, $R_{o2}$, $R_{o3}$. In this time, a difference between the number of sheets of the paper examined and that of the standard paper is related to a difference between the output electric signal delivered from the point linking output terminals of ultrasonic transducers $R_{s1}$, $R_{s2}$, $R_{s3}$ and that delivered from the point linking output terminals of ultrasonic transducers $R_{o1}$, $R_{o2}$, $R_{o3}$.

Figure 10:
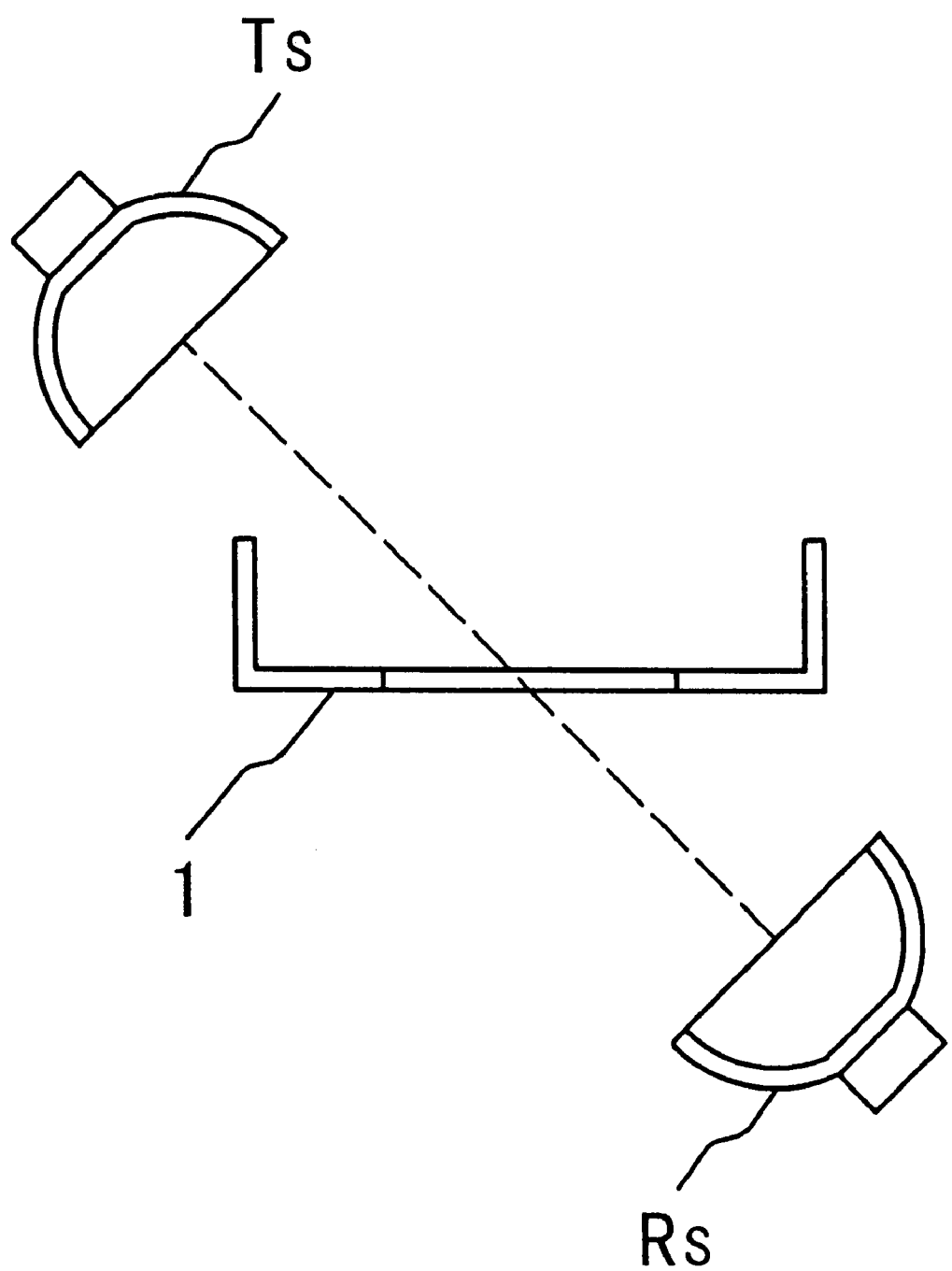
FIG. 10 shows a sectional view of an ultrasonic material constant measuring system according to a fourth embodiment of the present invention.

FIG. 10 shows a sectional view of an ultrasonic material constant measuring system according to a fourth embodiment of the present invention. The ultrasonic material constant measuring system comprises ultrasonic transducers $T_o$, $R_o$, $T_s$, $R_s$, case 1 placed between ultrasonic transducers $T_s$ and $R_s$, amplifier 2, and signal processing unit 3 comprising a differential amplifier. FIG. 10 shows only ultrasonic transducers $T_s$, $R_s$ and case 1. Both the distance between ultrasonic transducers $T_o$ and $R_o$, and the distance between ultrasonic transducers $T_s$ and $R_s$ are 4.95 cm. When operating, sheets of paper are placed in case 1 located such that the direction of an ultrasound going through the paper is oblique to an end surface of the paper. The relative position of ultrasonic transducer $T_o$ to ultrasonic transducer $R_o$ is equal to that of ultrasonic transducer $T_s$ to ultrasonic transducer $R_s$. Case 1 is not always placed between ultrasonic transducers $T_o$ and $R_o$.

When operating the ultrasonic material constant measuring system in FIG. 10, a driving circuit in FIG. 3 is employed. If electric signals are applied to ultrasonic transducers $T_o$ and $T_s$, respectively, ultrasounds are emitted in air from the cone centers of ultrasonic transducers $T_o$ and $T_s$, respectively. The ultrasounds are received by ultrasonic transducers $R_o$ and $R_s$, respectively, and delivered as output electric signals from ultrasonic transducer $R_o$ and $R_s$, respectively. If at least a sheet of paper is placed in case 1, the ultrasound emitted from ultrasonic transducer $T_s$ goes through the sheet of paper. Therefore, the output electric signal delivered from ultrasonic transducer $R_s$ is decreased, causing a difference between the output electric signals delivered from ultrasonic transducer $R_s$ and $R_o$. The difference is detected by signal processing unit 3 and compared with that corresponding to a standard paper. Thus, the thickness of the paper examined, or the number of sheets of the paper examined is evaluated.

An incidence angle of the ultrasound emitted from ultrasonic transducer $T_s$ to an end surface of a paper is 90° in FIG. 1, on the other hand, it is not 90° in FIG. 10. As a result, an ultrasound transmission rate to a paper in FIG. 10 is higher than that in FIG. 1. Therefore, the output electric signal delivered from ultrasonic transducer $R_s$ in FIG. 10 is higher than that in FIG. 1, causing the ultrasonic material constant measuring system in FIG. 10 to have a higher sensitivity than that in FIG. 1.

It is possible in FIG. 5 and FIG. 8 to change the situation of case 1 as FIG. 10. The direction of the ultrasound emitted from ultrasonic transducers $T_{s1}$, $T_{s2}$ and $T_{s3}$ is oblique to an end surface of the paper examined in the changed structure, causing a higher sensitive operation as compared with the original structure.

Figure 11:
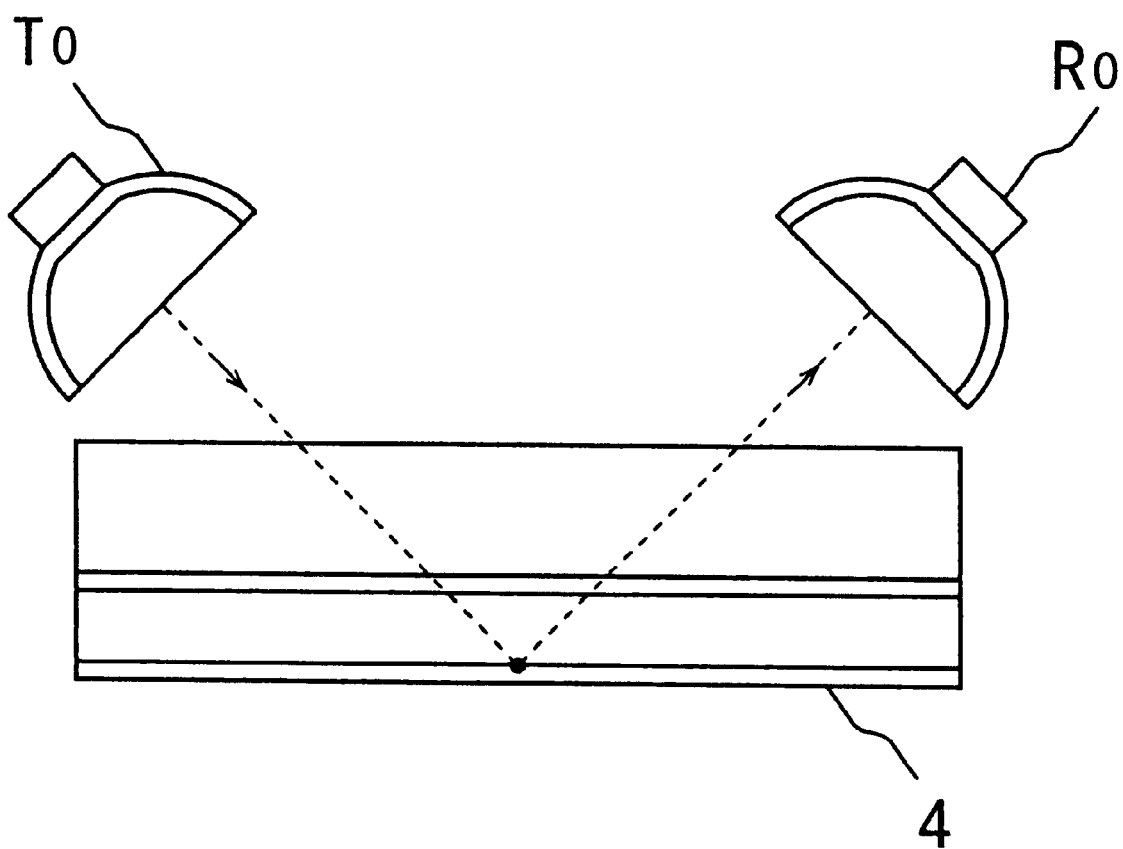
FIG. 11 shows a sectional view of an ultrasonic material constant measuring system according to a fifth embodiment of the present invention.

FIG. 11 shows a sectional view of an ultrasonic material constant measuring system according to a fifth embodiment of the present invention. The ultrasonic material constant measuring system comprises ultrasonic transducers $T_o$, $R_o$, $T_s$, $R_s$, amplifier 2, signal processing unit 3 comprising a differential amplifier, reference case 4 and examination case 5. FIG. 11 shows only ultrasonic transducers $T_o$, $R_o$ and reference case 4. Both reference case 4 and examination case 5 have the same structure and are made of the same material each other. The relative position of ultrasonic transducers $T_s$ and $R_s$ to examination case 5 is equal to that of ultrasonic transducers $T_o$ and $R_o$ to reference case 4.

Figure 12:
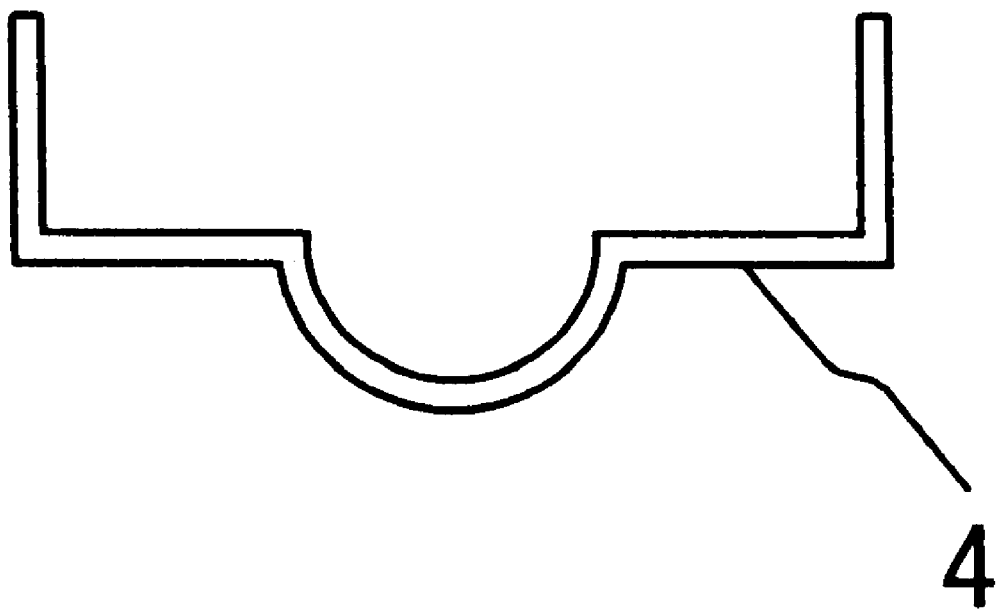
FIG. 12 shows a sectional view of reference case 4 viewed from a direction vertical to the section in FIG. 11.

FIG. 12 shows a sectional view of reference case 4 viewed from a direction vertical to the section in FIG. 11. Both reference case 4 and examination case 5 have concavities at the bottom of reference case 4 and examination case 5, respectively.

Figure 13:
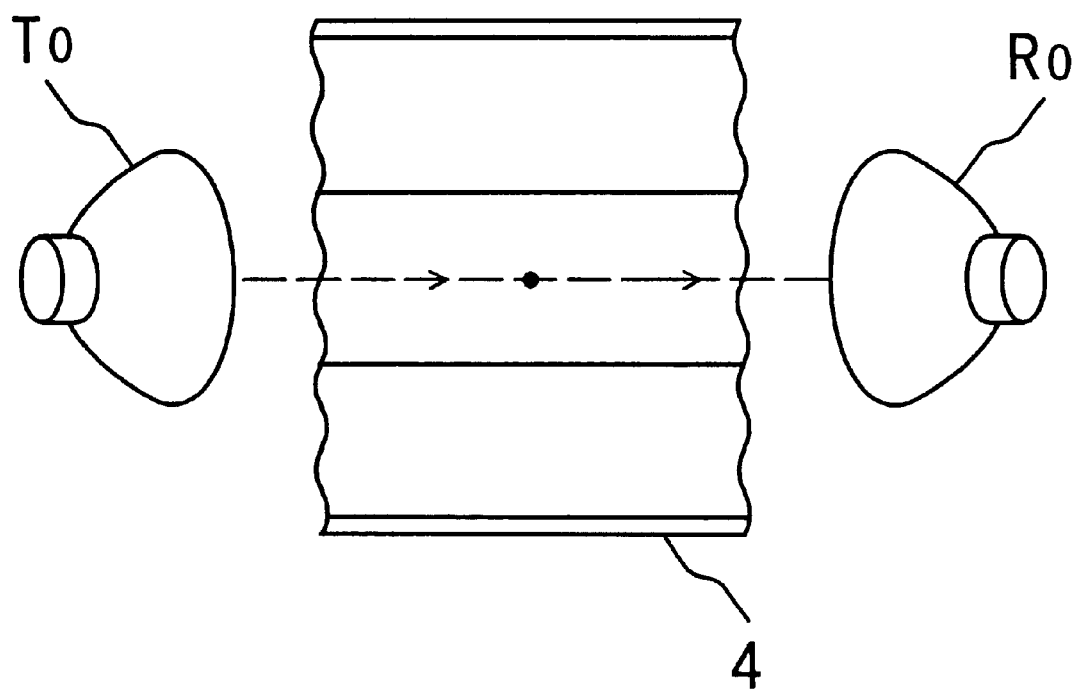
FIG. 13 shows a plan view of ultrasonic transducers $T_o$, $R_o$ and reference case 4 in FIG. 11 viewed from upside.

FIG. 13 shows a plan view of ultrasonic transducers $T_o$, $R_o$ and reference case 4 in FIG. 11 viewed from upside.

When operating the ultrasonic material constant measuring system in FIG. 11, a driving circuit having reference case 4 in place of case 1 between ultrasonic transducers $T_o$ and $R_o$, and having examination case 5 in place of case 1 between ultrasonic transducers $T_s$ and $R_s$ in FIG. 4 is employed. If an electric signal is applied to ultrasonic transducer $T_o$, an ultrasound is emitted in air from the cone center of ultrasonic transducer $T_o$. The ultrasound is reflected by the concavity at the bottom of reference case 4, and then received by ultrasonic transducer $R_o$, the ultrasound being delivered as an output electric signal from ultrasonic transducer $R_o$. In the same way, when an electric signal is applied to ultrasonic transducer $T_s$, an ultrasound is emitted in air from the cone center of ultrasonic transducer $T_s$, and is reflected by the concavity at the bottom of examination case 5, the ultrasound being received by ultrasonic transducer $R_s$ and delivered as an output electric signal from ultrasonic transducer $R_s$. If at least a sheet of paper is placed on the concavity of examination case 5, the ultrasound emitted from ultrasonic transducer $T_s$ goes through the sheet of paper twice. Therefore, the output electric signal delivered from ultrasonic transducer $R_s$ is decreased, causing a difference between the output electric signals delivered from ultrasonic transducer $R_s$ and $R_o$. The difference is detected by signal processing unit 3 and compared with that corresponding to a standard paper. Thus, the thickness of the paper examined, or the number of sheets of the paper examined is evaluated. If signal processing unit 3 comprises a phase comparator, the thickness of the paper examined, or the number of sheets of the paper examined is evaluated by comparing the phase difference with that corresponding to a standard paper. In the same way, if a leaf or a fiber is placed on the concavity of examination case 5, the thickness of the leaf or the diameter of the fiber is obtained, respectively. When sheets of examination paper and sheets of standard paper are placed on the concavities of examination case 5 and reference case 4, respectively, a difference between the number of sheets of the examination paper and that of the standard paper is related to a difference between the output electric signals delivered from ultrasonic transducer $R_s$ and $R_o$.

Figure 14:
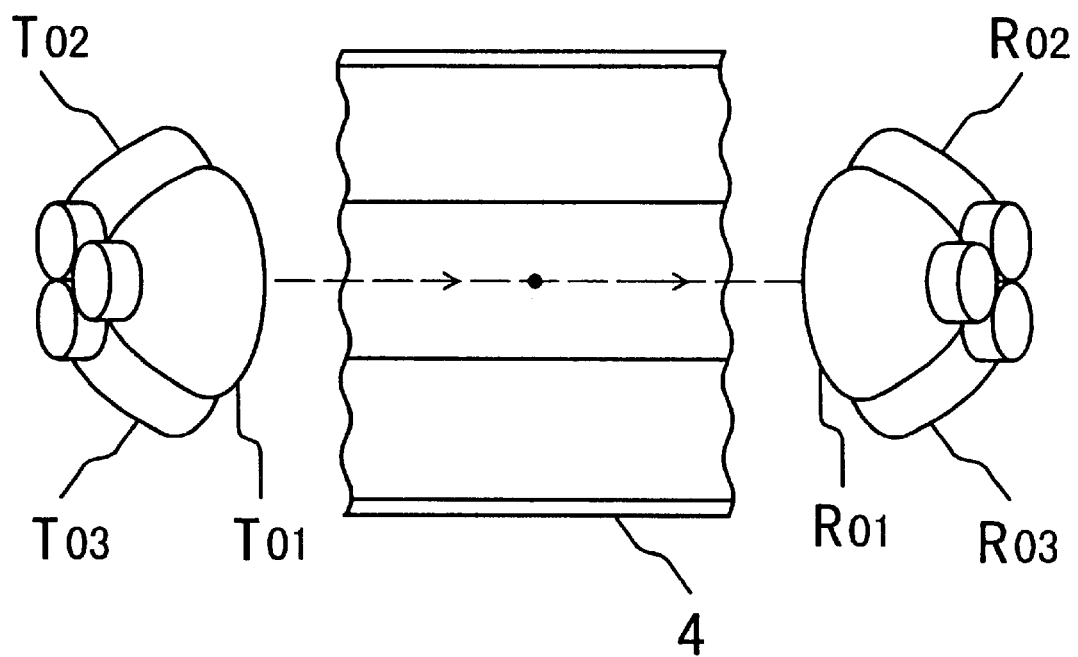
FIG. 14 shows a plan view of an ultrasonic material constant measuring system according to a sixth embodiment of the present invention.

FIG. 14 shows a plan view of an ultrasonic material constant measuring system according to a sixth embodiment of the present invention. The ultrasonic material constant measuring system comprises ultrasonic transducers $T_{o1}$, $T_{o2}$, $T_{o3}$, $T_{s1}$, $T_{s2}$, $T_{s3}$, $R_{o1}$, $R_{o2}$, $R_{o3}$, $R_{s1}$, $R_{s2}$, $R_{s3}$, amplifier 2, signal processing unit 3 comprising a differential amplifier, reference case 4 and examination case 5. FIG. 14 shows only ultrasonic transducers $T_{o1}$, $T_{o2}$, $T_{o3}$, $R_{o1}$, $R_{o2}$, $R_{o3}$ and reference case 4 viewed from upside. Three gravity centers of ultrasonic transducers $T_{o1}$, $T_{o2}$ and $T_{o3}$, three gravity centers of ultrasonic transducers $R_{o1}$, $R_{o2}$ and $R_{o3}$, three gravity centers of ultrasonic transducers $T_{s1}$, $T_{s2}$ and $T_{s3}$, and three gravity centers of ultrasonic transducers $R_{s1}$, $R_{s2}$ and $R_{s3}$ make triangles, respectively. The relative position of ultrasonic transducers $T_{s1}$, $T_{s2}$, $T_{s3}$, $R_{s1}$, $R_{s2}$ and $R_{s3}$ to examination case 5 is equal to that of ultrasonic transducers $T_{o1}$, $T_{o2}$, $T_{o3}$ $R_{o1}$, $R_{o2}$ and $R_{o3}$ to reference case 4.

When operating the ultrasonic material constant measuring system in FIG. 14, a driving circuit having reference case 4 between ultrasonic transducers $T_{o1}$, $T_{o2}$, $T_{o3}$ and ultrasonic transducers $R_{o1}$, $R_{o2}$ and $R_{o3}$, and having examination case 5 in place of case 1 between ultrasonic transducers Ts1, Ts2, Ts3 and ultrasonic transducers $R_{s1}$, $R_{s2}$ and $R_{s3}$ in FIG. 9 is employed. If electric signals are applied to ultrasonic transducers $T_{o1}$, $T_{o2}$ and $T_{o3}$, respectively, an ultrasound with a sharp directionality is emitted in air from the center of the triangle made by ultrasonic transducers $T_{o1}$, $T_{o2}$ and $T_{o3}$. The ultrasound is reflected by the concavity of reference case 4, and then received by ultrasonic transducers $R_{o1}$, $R_{o2}$ and $R_{o3}$, the ultrasound being delivered as an output electric signal from a point linking output terminals of ultrasonic transducers $R_{o1}$, $R_{o2}$ and $R_{o3}$. In this time, ultrasonic transducers $T_{o1}$, $T_{o2}$ and $T_{o3}$ has an ability to emit an ultrasound with a sharp directionality centered on the center of the triangle made by ultrasonic transducers $T_{o1}$, $T_{o2}$ and $T_{o3}$, and ultrasonic transducers $R_{o1}$, $R_{o2}$ and $R_{o3}$ has an ability to receive an ultrasound with a sharp directionality centered on the center of the triangle made by ultrasonic transducers $R_{o1}$, $R_{o2}$ and $R_{o3}$. Reference case 4 is placed at the area where the ultrasound emitted from ultrasonic transducers $T_{o1}$, $T_{o2}$ and $T_{o3}$ is most sharply and most strongly. In the same way, when electric signals are applied to ultrasonic transducers $T_{s1}$, $T_{s2}$ and $T_{s3}$, respectively, an ultrasound with a sharp directionality is emitted in air from the center of the triangle made by ultrasonic transducers $T_{s1}$, $T_{s2}$ and $T_{s3}$. The ultrasound is reflected by the concavity of examination case 5, and then received by ultrasonic transducers $R_{s1}$, $R_{s2}$ and $R_{s3}$, the ultrasound being delivered as an output electric signal from a point linking output terminals of ultrasonic transducers $R_{s1}$, $R_{s2}$ and $R_{s3}$. In this time, ultrasonic transducers $T_{s1}$, $T_{s2}$ and $T_{s3}$ has an ability to emit an ultrasound with a sharp directionality centered on the center of the triangle made by ultrasonic transducers $T_{s1}$, $T_{s2}$ and $T_{s3}$, and ultrasonic transducers $R_{s1}$, $R_{s2}$ and $R_{s3}$ has an ability to receive an ultrasound with a sharp directionality centered on the center of the triangle made by ultrasonic transducers $R_{s1}$, $R_{s2}$ and $R_{s3}$. Examination case 5 is placed at the area where the ultrasound emitted from ultrasonic transducers $T_{s1}$, $T_{s2}$ and $T_{s3}$ is most sharply and most strongly. If at least a sheet of paper is placed on the concavity of examination case 5, the ultrasound emitted from ultrasonic transducers $T_{s1}$, $T_{s2}$ and $T_{s3}$ goes through the sheet of paper twice. Therefore, the output electric signal delivered from the point linking output terminals of ultrasonic transducers $R_{s1}$, $R_{s2}$ and $R_{s3}$ is decreased, causing a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$. The difference is detected by signal processing unit 3 and compared with that corresponding to a standard paper. Thus, the thickness of the paper examined, or the number of sheets of the paper examined is evaluated. If signal processing unit 3 comprises a phase comparator, the thickness of the paper examined, or the number of sheets of the paper examined is evaluated by comparing the phase difference with that corresponding to a standard paper. The ultrasonic material constant measuring system in FIG. 14 enables a higher sensitive operation under a low voltage in comparison with that in FIG. 11, because of input ultrasonic transducers emitting an ultrasound with a sharp directionality, and output ultrasonic transducers receiving an ultrasound with a sharp directionality. When sheets of examination paper and sheets of standard paper are placed on the concavities of examination case 5 and reference case 4, respectively, a difference between the number of sheets of the examination paper and that of the standard paper is related to a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$.

Figure 15:
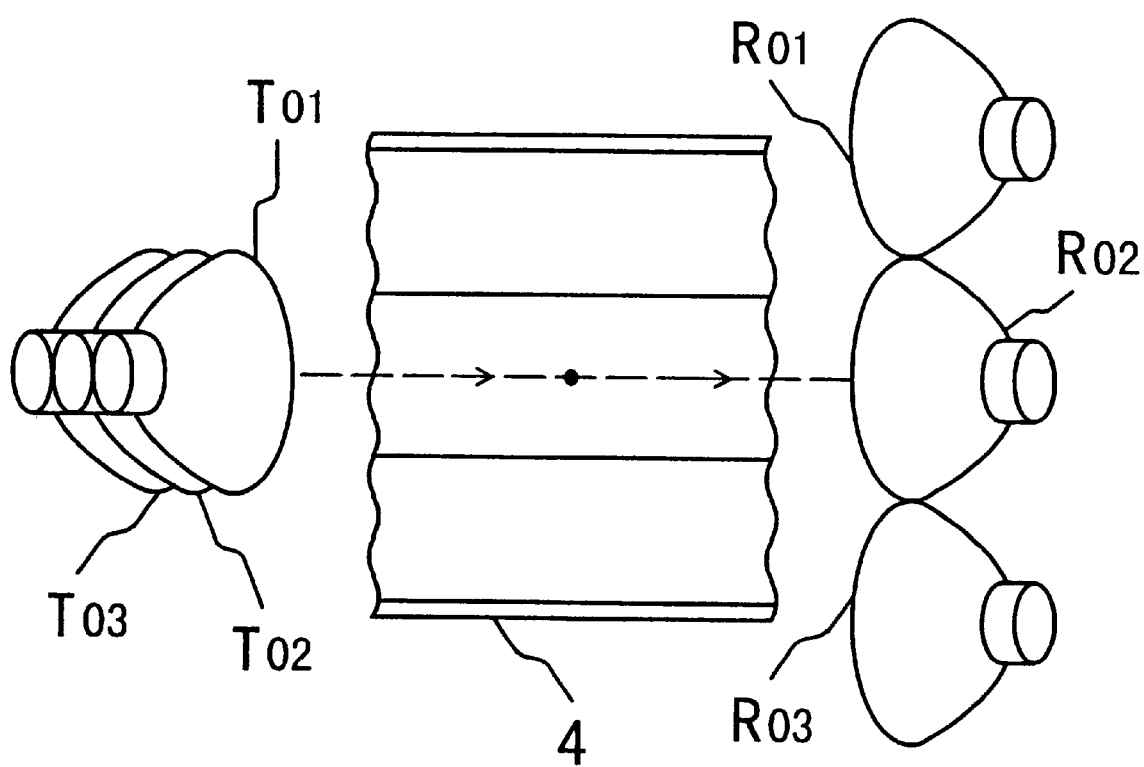
FIG. 15 shows a plan view of an ultrasonic material constant measuring system according to a seventh embodiment of the present invention.

FIG. 15 shows a plan view of an ultrasonic material constant measuring system according to a seventh embodiment of the present invention. The ultrasonic material constant measuring system comprises ultrasonic transducers $T_{o1}$, $T_{o2}$, $T_{o3}$, $T_{s1}$, $T_{s2}$, $T_{s3}$, $R_{o1}$, $R_{o2}$, $R_{o3}$, $R_{s1}$, $R_{s2}$, $R_{s3}$, amplifier 2, signal processing unit 3 comprising a differential amplifier, reference case 4 and examination case 5. FIG. 15 shows only ultrasonic transducers $T_{o1}$, $T_{o2}$, $T_{o3}$, $R_{o1}$, $R_{o2}$, $R_{o3}$ and reference case 4 viewed from upside. Ultrasonic transducers $T_{o1}$, $T_{o2}$ and $T_{o3}$ are arranged such that three gravity centers thereof make a straight line, and ultrasonic transducers $R_{o1}$, $R_{o2}$, $R_{o3}$ are arranged such that three gravity centers thereof make a straight line. The straight line made by ultrasonic transducers $T_{o1}$, $T_{o2}$ and $T_{o3}$ is vertical to the straight line made by ultrasonic transducers $R_{o1}$, $R_{o2}$ and $R_{o3}$. Ultrasonic transducers $T_{s1}$, $T_{s2}$ and $T_{s3}$ are arranged such that three gravity centers thereof make a straight line, and ultrasonic transducers $R_{s1}$, $R_{s2}$ and $R_{s3}$ are arranged such that three gravity centers thereof make a straight line. The straight line made by ultrasonic transducers $T_{s1}$, $T_{s2}$ and $T_{s3}$ is vertical to the straight line made by ultrasonic transducers $R_{s1}$, $R_{s2}$ and $R_{s3}$. The relative position of ultrasonic transducers $T_{s1}$, $T_{s2}$, $T_{s3}$, $R_{s1}$, $R_{s2}$ and $R_{s3}$ to examination case 5 is equal to that of ultrasonic transducers $T_{o1}$, $T_{o2}$, $T_{o3}$, $R_{o1}$, $R_{o2}$ and $R_{o3}$ to reference case 4.

When operating the ultrasonic material constant measuring system in FIG. 15, a driving circuit having reference case 4 between ultrasonic transducers $T_{o1}$, $T_{o2}$, $T_{o3}$ and ultrasonic transducers $R_{o1}$, $R_{o2}$ and $R_{o3}$, and having examination case 5 in place of case 1 between ultrasonic transducers $T_{s1}$, $T_{s2}$, $T_{s3}$ and ultrasonic transducers $R_{s1}$, $R_{s2}$ and $R_{s3}$ in FIG. 9 is employed. If electric signals are applied to ultrasonic transducers $T_{o1}$, $T_{o2}$ and $T_{o3}$, respectively, an ultrasound with a sharp directionality is emitted in air from the center of the straight line made by ultrasonic transducers $T_{o1}$, $T_{o2}$ and $T_{o3}$. The ultrasound is reflected by the concavity of reference case 4, and then received by ultrasonic transducers $R_{o1}$, $R_{o2}$ and $R_{o3}$, the ultrasound being delivered as an output electric signal from a point linking output terminals of ultrasonic transducers $R_{o1}$, $R_{o2}$ and $R_{o3}$. In this time, ultrasonic transducers $T_{o1}$, $T_{o2}$ and $T_{o3}$ has an ability to emit an ultrasound with a directionality on a surface including the concavity of reference case 4 and two gravity centers of ultrasonic transducers $T_{o1}$, and $T_{o3}$, and ultrasonic transducers $R_{o1}$, $R_{o2}$ and $R_{o3}$ has an ability to receive an ultrasound with a directionality on a surface including the concavity of reference case 4 and two gravity centers of ultrasonic transducers $R_{o1}$ and $R_{o3}$, Reference case 4 is placed at the area where the ultrasound emitted from ultrasonic transducers $T_{o1}$, $T_{o2}$ and $T_{o3}$ is most sharply and most strongly. In the same way, when electric signals are applied to ultrasonic transducers $T_{s1}$, $T_{s2}$ and $T_{s3}$, respectively, an ultrasound with a sharp directionality is emitted in air from the center of the straight line made by ultrasonic transducers $T_{s1}$, $T_{s2}$ and $T_{s3}$. The ultrasound is reflected by the concavity of examination case 5, and then received by ultrasonic transducers $R_{s1}$, $R_{s2}$ and $R_{s3}$, the ultrasound being delivered as an output electric signal from a point linking output terminals of ultrasonic transducers $R_{s1}$, $R_{s2}$ and $R_{s3}$. In this time, ultrasonic transducers $T_{s1}$, $T_{s2}$ and $T_{s3}$ has an ability to emit an ultrasound with a directionality on a surface including the concavity of examination case 5 and two gravity centers of ultrasonic transducers $T_{s1}$, and $T_{s3}$, and ultrasonic transducers $R_{s1}$, $R_{s2}$ and $R_{s3}$ has an ability to receive an ultrasound with a directionality on a surface including the concavity of examination case 5 and two gravity centers of ultrasonic transducers $R_{s1}$, and $R_{s3}$. Examination case 5 is placed at the area where the ultrasound emitted from ultrasonic transducers $T_{s1}$, $T_{s2}$ and $T_{s3}$ is most sharply and most strongly. If at least a sheet of paper is placed on the concavity of examination case 5, the ultrasound emitted from ultrasonic transducers $T_{s1}$, $T_{s2}$ and $T_{s3}$ goes through the sheet of paper twice. Therefore, the output electric signal delivered from the point linking output terminals of ultrasonic transducers $R_{s1}$, $R_{s2}$ and $R_{s3}$ is decreased, causing a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$. The difference is detected by signal processing unit 3 and compared with that corresponding to a standard paper. Thus, the thickness of the paper examined, or the number of sheets of the paper examined is evaluated. If signal processing unit 3 comprises a phase comparator, the thickness of the paper examined, or the number of sheets of the paper examined is evaluated by comparing the phase difference with that corresponding to a standard paper. The ultrasonic material constant measuring system in FIG. 15 enables a higher sensitive operation under a low voltage in comparison with that in FIG. 11, because of input ultrasonic transducers emitting an ultrasound with a sharp directionality, and output ultrasonic transducers receiving an ultrasound with a sharp directionality. When sheets of examination paper and sheets of standard paper are placed on the concavities of examination case 5 and reference case 4, respectively, a difference between the number of sheets of the examination paper and that of the standard paper is related to a difference between the output electric signal delivered from the point linking output terminals of ultrasonic transducers $R_{s1}$, $R_{s2}$ and $R_{s3}$ and that delivered from the point linking output terminals of ultrasonic transducers $R_{o1}$, $R_{o2}$ and $R_{o3}$.

Figure 16:
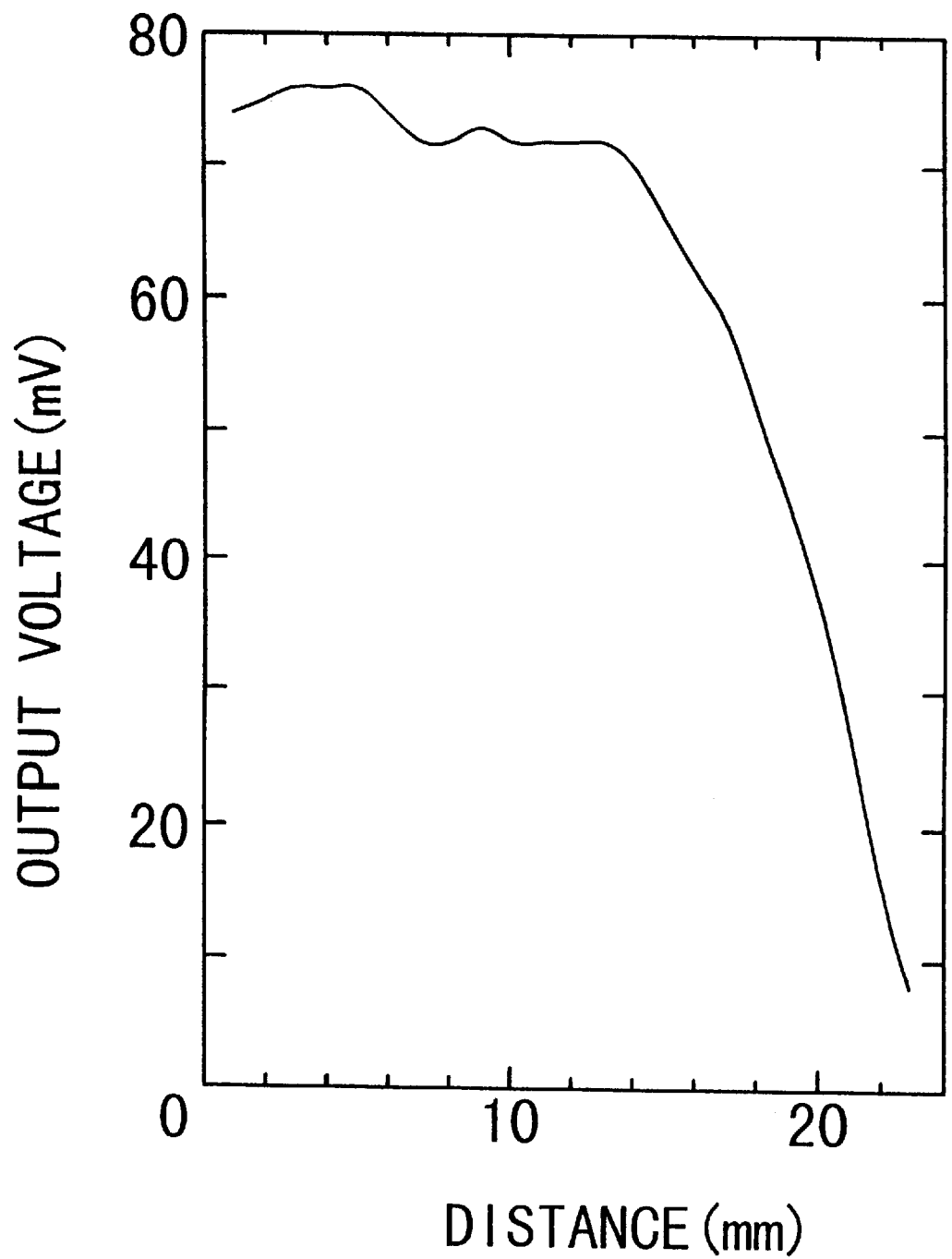
FIG. 16 shows a relationship between the output electric signal at ultrasonic transducer $R_s$ and the moving distance of ultrasonic transducer $R_s$ from the initial position to a position along a line including the initial position and vertical to the direction of the ultrasound emitted from ultrasonic transducer $T_s$ in the ultrasonic material constant measuring system in FIG. 1.

FIG. 16 shows a relationship between the output electric signal at ultrasonic transducer $R_s$ and the moving distance of ultrasonic transducer $R_s$ from the initial position to a position along a line including the initial position and vertical to the direction of the ultrasound emitted from ultrasonic transducer $T_s$ in the ultrasonic material constant measuring system in FIG. 1. The moving distance is zero mm when ultrasonic transducer $R_s$ is right in front of ultrasonic transducer $T_s$ as in FIG. 1. An electric signal with 120 mV is applied to ultrasonic transducer $T_s$. It is clear from FIG. 16 that the ultrasound emitted from ultrasonic transducer $T_s$ is received by ultrasonic transducer $R_s$ effectively when the moving distance is under 14 mm. In other words, the ultrasound with the diameter under 28 mm goes through sheets of paper effectively. Thus, case 1 has the opening at the top thereof, as shown in FIG. 2, for the purpose of ultrasound transmission.

Figure 17:
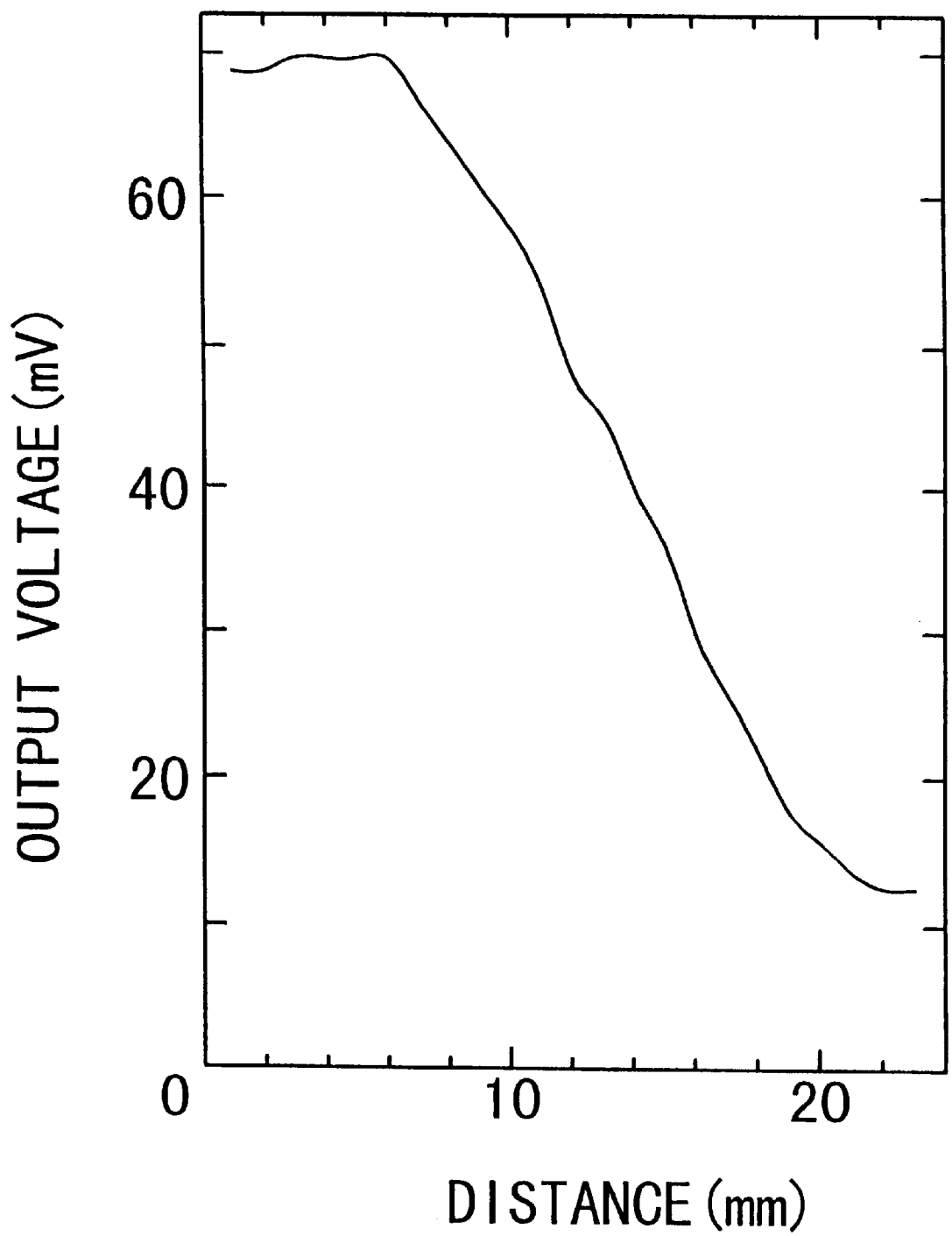
FIG. 17 shows a relationship between the output electric signal at ultrasonic transducer $R_o$ and the moving distance of ultrasonic transducer $R_s$ from the initial position to a position along a line including the initial position and vertical to the direction of the ultrasound emitted from ultrasonic transducers $T_{s1}$, $T_{s2}$ and $T_{s3}$ in the ultrasonic material constant measuring system in FIG. 5.

FIG. 17 shows a relationship between the output electric signal at ultrasonic transducer $R_s$ and the moving distance of ultrasonic transducer $R_s$ from the initial position to a position along a line including the initial position and vertical to the direction of the ultrasound emitted from ultrasonic transducers $T_{s1}$, $T_{s2}$ and $T_{s3}$ in the ultrasonic material constant measuring system in FIG. 5. The moving distance is zero mm when ultrasonic transducer $R_s$ is right in front of the center of the triangle made by ultrasonic transducers $T_{o1}$, $T_{o2}$ and $T_{o3}$ as in FIG. 5. Electric signals with 40.8 mV are applied to ultrasonic transducers $T_{s1}$, $T_{s2}$ and $T_{s3}$, respectively. It is clear from FIG. 17 that the ultrasound emitted from ultrasonic transducers $T_{o1}$, $T_{o2}$ and $T_{o3}$ is received by ultrasonic transducer $R_s$ effectively when the moving distance is under 6 mm. In other words, the ultrasound with the diameter under 12 mm goes through sheets of paper effectively. In addition, it is clear from FIGS. 16 and 17 that the ultrasound emitted from ultrasonic transducers $T_{o1}$, $T_{o2}$ and $T_{o3}$ in FIG. 5 has a sharp directionality in comparison with that emitted from ultrasonic transducer $T_s$ in FIG. 1.

Figure 18:
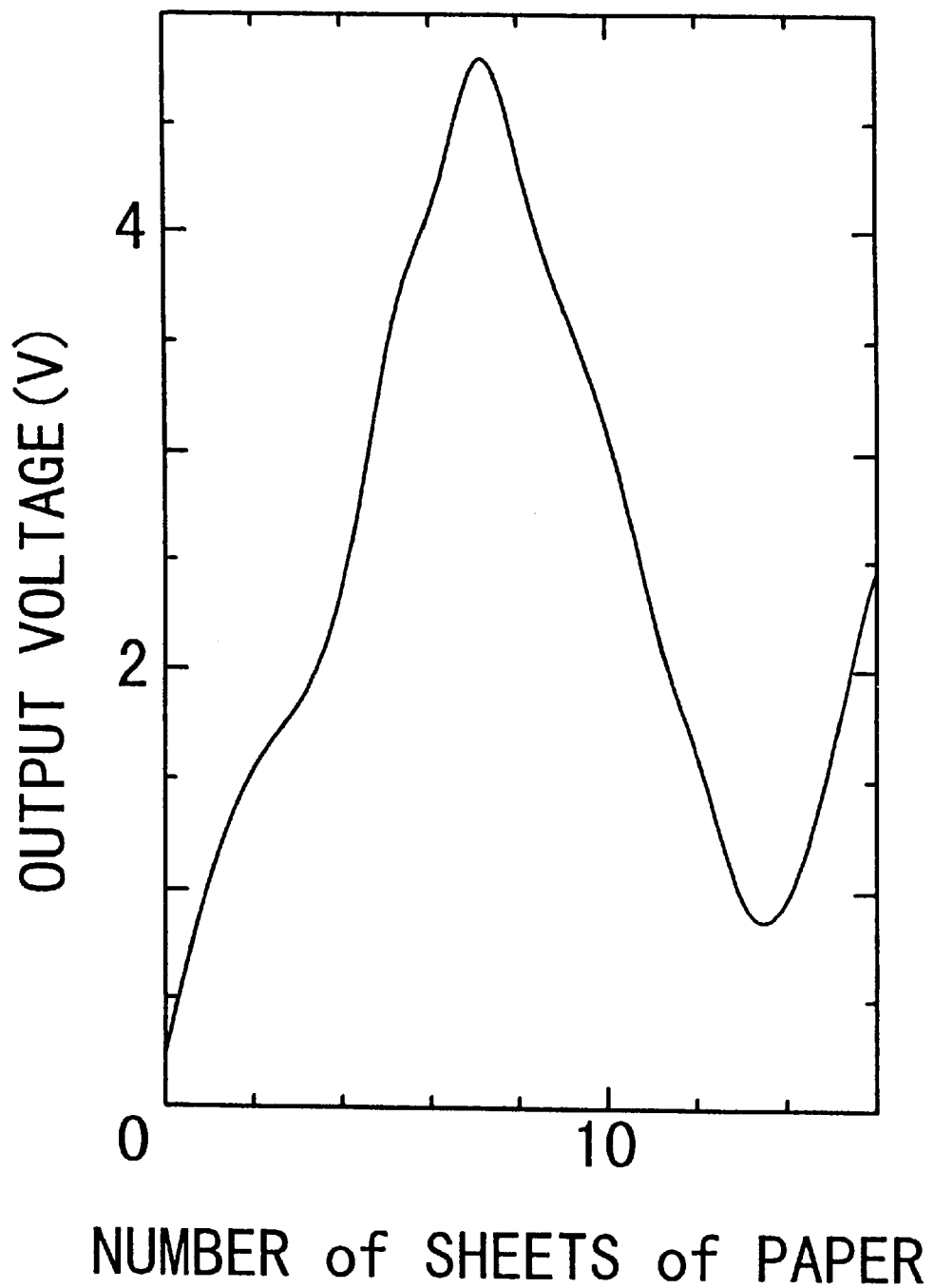
FIG. 18 shows a relationship between number of sheets of paper in case 1, and an output voltage as a difference between output electric signals delivered from ultrasonic transducers $R_s$ and $R_o$ in the ultrasonic material constant measuring system in FIG. 1.

FIG. 18 shows a relationship between number of sheets of paper in case 1, and an output voltage as a difference between output electric signals delivered from ultrasonic transducers $R_s$ and $R_o$ in the ultrasonic material constant measuring system in FIG. 1. There are two values on the x-axis at a value on the y-axis under some cases. However, the first value on the x-axis is on the upward line, on the other hand, the second value on the x-axis is on the downward line. Therefore, the first and the second values on the x-axis at a value on the y-axis are distinguished. Thus, the number of sheets of paper is obtained by one output voltage and the other output voltage in front or in rear thereof.

Figure 19:
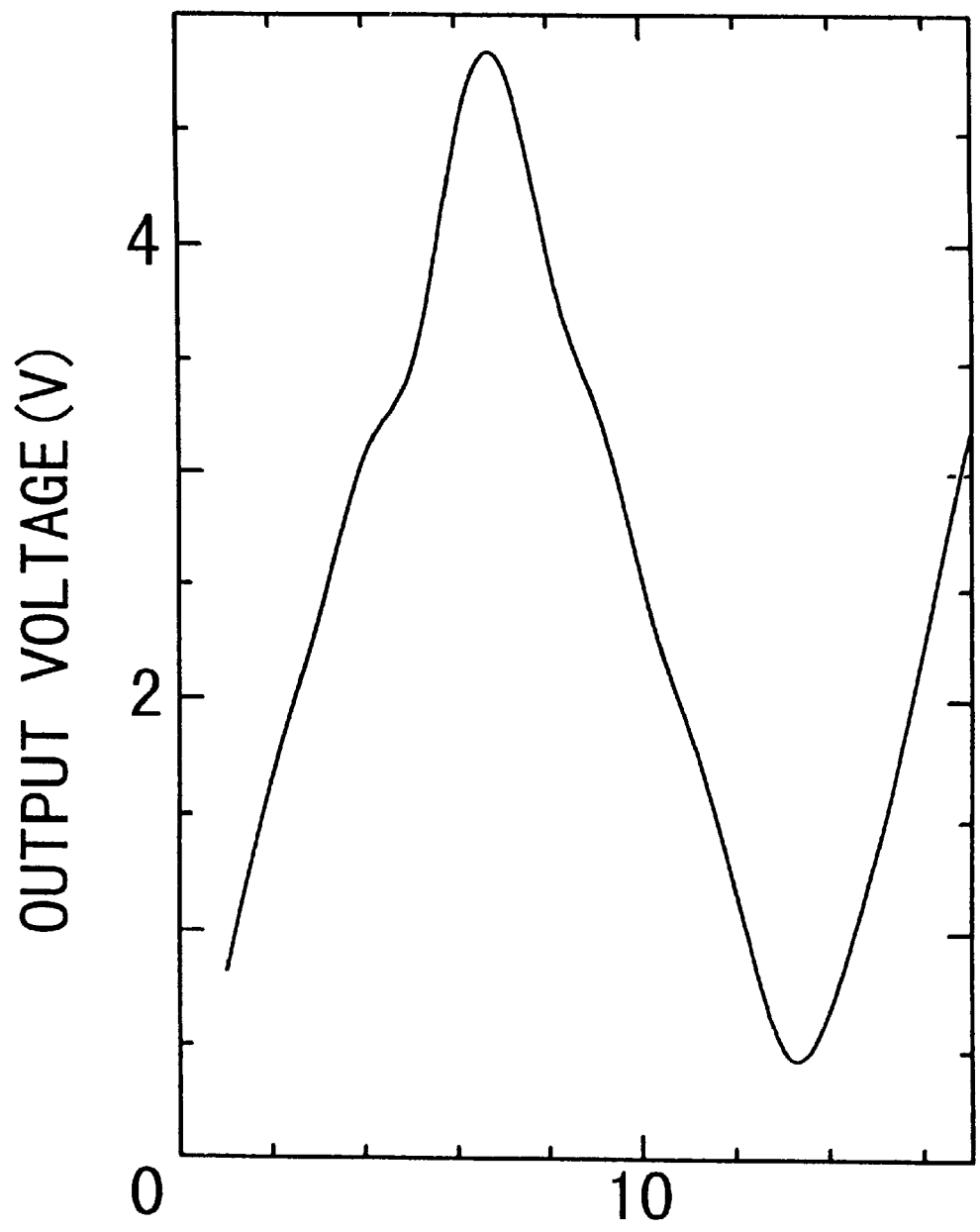
FIG. 19 shows a relationship between number of sheets of paper in case 1, and an output voltage as a difference between output electric signals delivered from ultrasonic transducers $R_s$ and $R_o$ in the ultrasonic material constant measuring system in FIG. 5.

FIG. 19 shows a relationship between number of sheets of paper in case 1, and an output voltage as a difference between output electric signals delivered from ultrasonic transducers $R_s$ and $R_o$ in the ultrasonic material constant measuring system in FIG. 5. The increasing rate or decreasing rate in output voltage to number of sheets of paper in FIG. 19 is larger than that in FIG. 18. Therefore, the ultrasonic material constant measuring system in FIG. 5 has a higher sensitivity than that in FIG. 1.

Figure 20:
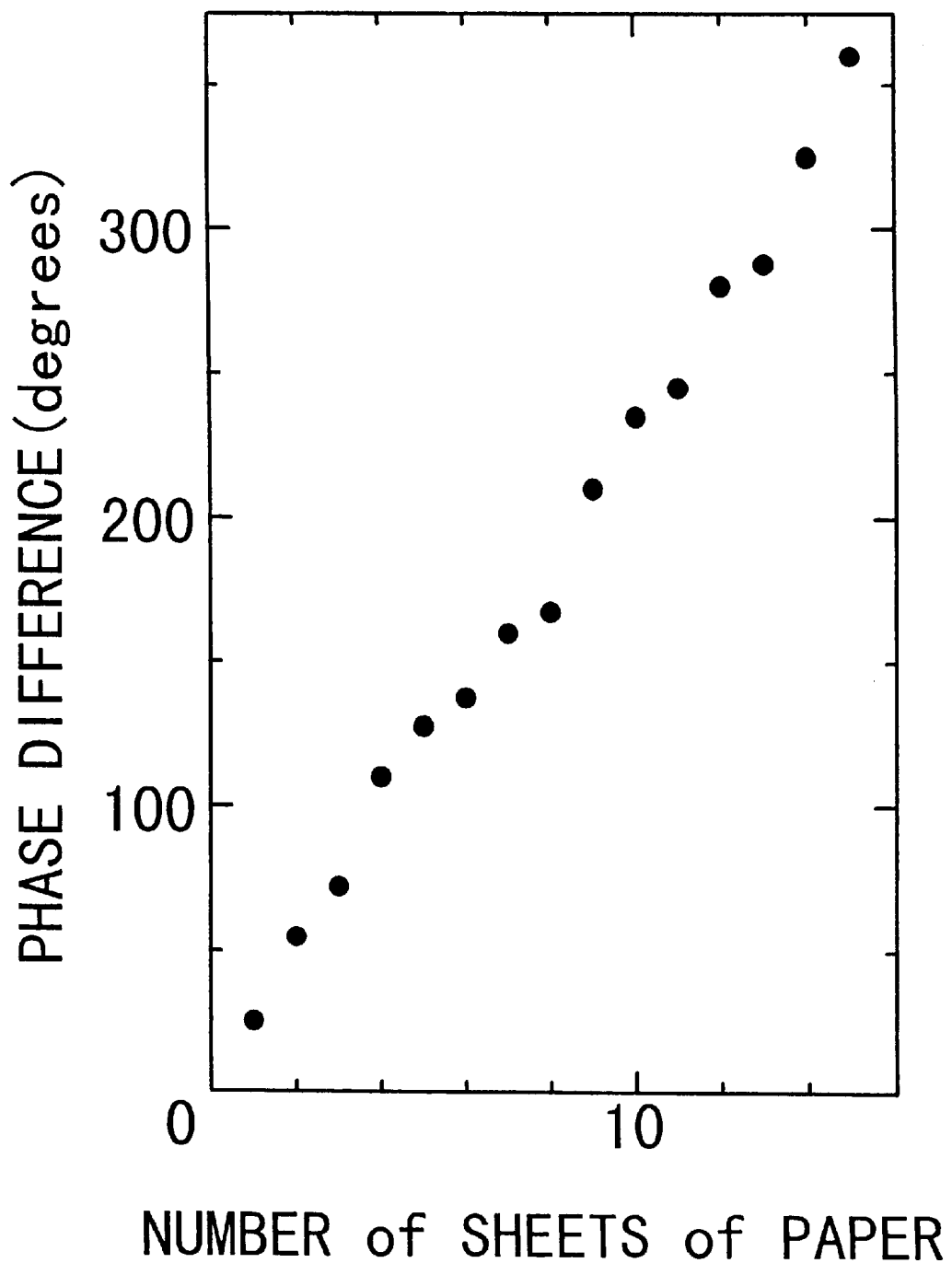
FIG. 20 shows a relationship between number of sheets of paper in case 1, and a phase difference between output electric signals delivered from ultrasonic transducers $R_s$ and $R_o$ in the ultrasonic material constant measuring system in FIG. 1.

FIG. 20 shows a relationship between number of sheets of paper in case 1, and a phase difference between output electric signals delivered from ultrasonic transducers $R_s$ and $R_o$ in the ultrasonic material constant measuring system in FIG. 1. According to increase in number of sheets of paper, the phase difference increases.

Figure 21:
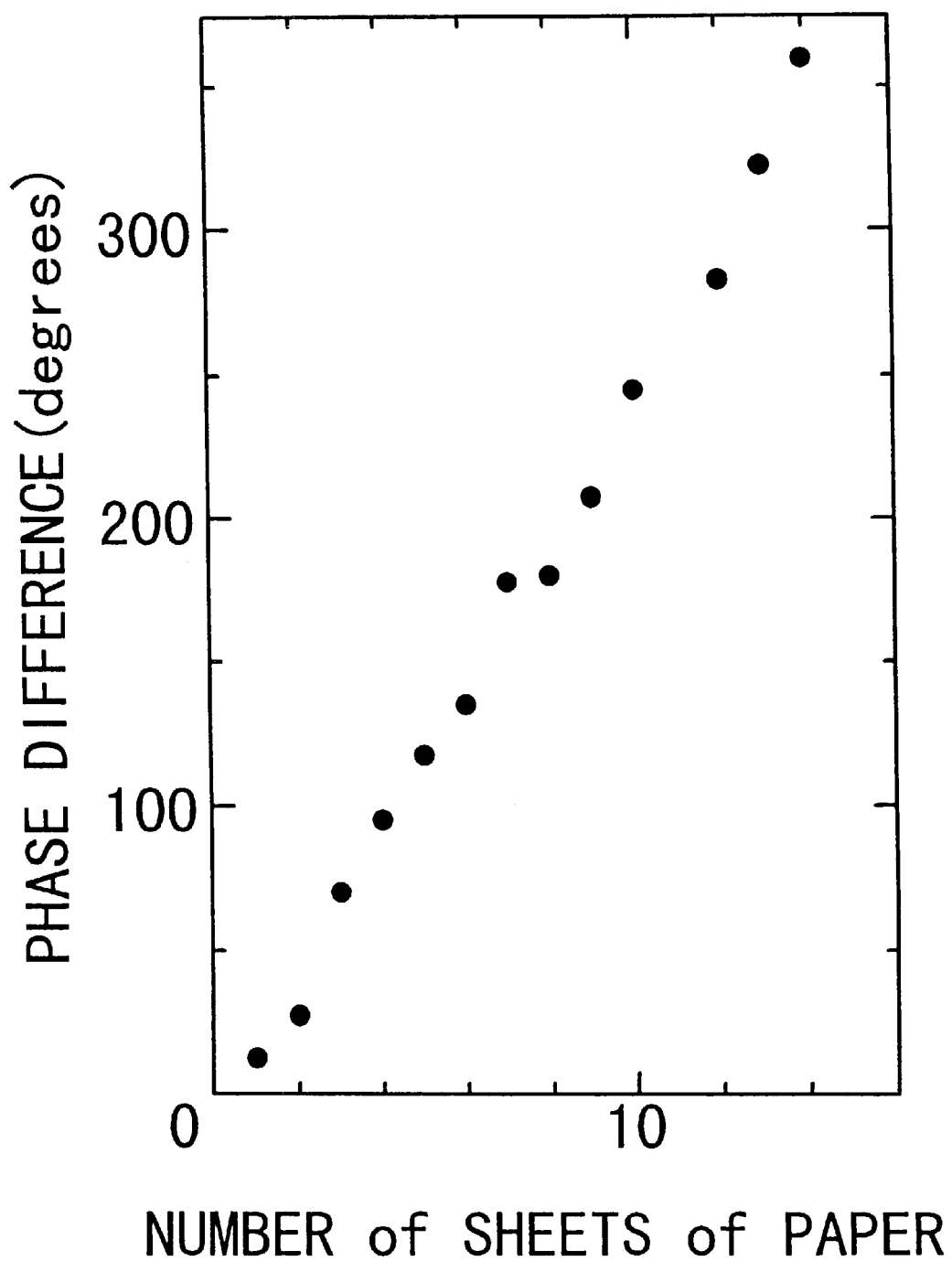
FIG. 21 shows a relationship between number of sheets of paper in case 1, and a phase difference between output electric signals delivered from ultrasonic transducers $R_s$ and $R_o$ in the ultrasonic material constant measuring system in FIG. 5.

FIG. 21 shows a relationship between number of sheets of paper in case 1, and a phase difference between output electric signals delivered from ultrasonic transducers $R_s$ and $R_o$ in the ultrasonic material constant measuring system in FIG. 5. The increasing rate in phase difference to number of sheets of paper in FIG. 21 is larger than that in FIG. 20. Therefore, the ultrasonic material constant measuring system in FIG. 5 has a higher sensitivity than that in FIG. 1.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. An ultrasonic material constant measuring system comprising:
    a reference unit consisting of
        (a) at least two reference input ultrasonic transducers, and
        (b) at least two reference output ultrasonic transducers, wherein a straight line including the gravity centers of said reference input transducers is vertical to a straight line including the gravity centers of said reference output transducers;
    an examination unit consisting of
        (a) at least two examination input ultrasonic transducers, and
        (b) at least two examination output ultrasonic transducers, wherein a straight line including the gravity centers of said examination input transducers is vertical to a straight line including the gravity centers of said examination output transducers;
    at least on case equipped in at least said examination unit, said at least one case being placed between said examination input transducers and said examination output transducer, and having at least one sheet of examination paper, at least one examination leaf, or an examination fiber therein; and
    a signal processing unit connected with a reference point linking the output terminals of said reference output transducers, said signal processing unit also connected with an examination point linking the output terminals of said examination output transducers;

said reference input transducers receiving first electric signals, respectively transducing said first electric signals to a first ultrasound with a sharp directionality, and emitting said first ultrasound in air, said reference output transducers receiving said first ultrasound emitted from said reference input transducers and transducing said first ultrasound to first reference output electric signals, said examination input transducers receiving second electric signals, respectively transducing said second electric signals to a second ultrasound with a sharp directionality, emitting said second ultrasound in air and through said at least one examination paper, said at least one examination leaf, or said examination fiber, said at least one case being placed at the area where said second ultrasound emitted from said examination input transducers is most sharply and most strongly defined, said examination output transducers receiving said second ultrasound transmitted through said at least one examination paper, said at least one examination leaf, or said examination fiber, and transducing said second ultrasound to first examination output electric signals, said signal processing unit detecting a difference between a second reference output electric signal delivered from said reference point linking the output terminals of said reference output transducers and a second examination output electric signal delivered from said examination point linking the output terminals of said examination output transducers, comparing said difference with that corresponding to a standard paper, a standard leaf, or a standard fiber, and evaluating from the comparison the thickness of a sheet of said at least one examination paper, the number of sheets of said at least one examination paper, the thickness of said at least one examination leaf or the diameter of said examination fiber.

2. An ultrasonic material constant measuring system as defined in claim 1 further comprising an amplifier, wherein said reference point linking the output terminals of said reference output transducers is connected with the input terminals of said reference and examination input transducers via said amplifier, and said reference input and output transducers and said amplifier form an oscillator with an ultrasonic propagation lane, as a delay element, between said reference input transducers and said reference output transducer.

3. An ultrasonic material constant measuring system as defined in claim 1, wherein said signal processing unit a phase comparator, said phase comparator detecting a phase difference between said second reference output electric signal delivered from said point linking the output terminals of said reference output transducers and said examination output electric signal delivered from said examination point linking the output terminals of said examination output transducers, comparing said phase difference with that corresponding to a standard paper, a standard leaf, or a standard fiber, and evaluating from the comparison the thickness of a sheet of said at least one examination paper, the number of sheets of said at least one examination paper, the thickness of said at least one examination leaf, or the diameter of said examination fiber.

4. An ultrasonic material constant measuring system as defined in claim 1, wherein the direction of said second ultrasound emitted from said examination input transducers is oblique to the end surface of said at least one examination paper, the end surface of said at least one examination leaf, or the longitudinal axis of said examination fiber.

* * * * *